(12) United States Patent
Wu et al.

(10) Patent No.: US 9,085,520 B2
(45) Date of Patent: Jul. 21, 2015

(54) COMPOSITION FOR TREATING DIABETES AND METABOLIC DISEASES AND A PREPARATION METHOD THEREOF

(75) Inventors: Yang-Chang Wu, Kaohsiung (TW); Fang-Rong Chang, Kaohsiung (TW); Tusty-Jiuan Hsieh, Kaohsiung (TW); Ying-Chi Du, Chiayi (TW); Yi-Hong Tsai, Kaohsiung (TW); Chi-Ting Hsieh, Changhua County (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 14/237,724

(22) PCT Filed: Aug. 8, 2012

(86) PCT No.: PCT/US2012/049968
§ 371 (c)(1),
(2), (4) Date: Aug. 8, 2014

(87) PCT Pub. No.: WO2013/022951
PCT Pub. Date: Feb. 14, 2013

(65) Prior Publication Data
US 2014/0350304 A1    Nov. 27, 2014

(30) Foreign Application Priority Data
Aug. 10, 2011  (TW) .............................. 100128615 A

(51) Int. Cl.
| C07C 49/00 | (2006.01) |
| A61K 31/12 | (2006.01) |
| C07C 49/84 | (2006.01) |
| C07C 49/796 | (2006.01) |
| C07C 49/835 | (2006.01) |
| C07D 317/54 | (2006.01) |

(52) U.S. Cl.
CPC ................. *C07C 49/84* (2013.01); *A61K 31/12* (2013.01); *C07C 49/796* (2013.01); *C07C 49/835* (2013.01); *C07D 317/54* (2013.01)

(58) Field of Classification Search
CPC .... C07C 49/84; C07C 49/795; C07C 49/835; A61K 31/12
USPC .......................................... 568/334; 514/679
See application file for complete search history.

(56) References Cited

U.S. PATENT DOCUMENTS

| 7,888,388 B2 | 2/2011 | Mae et al. |
| 2006/0286182 A1 | 12/2006 | Patel |
| 2007/0092551 A1* | 4/2007 | Enoki et al. ................... 424/439 |
| 2009/0176718 A1 | 7/2009 | Ribnicky et al. |

FOREIGN PATENT DOCUMENTS

WO    2009026658    3/2009

OTHER PUBLICATIONS

Hsieh et al., "Synthesis of chalcone derivatives as potential antidiabetic agents," Bioorganic & Medicinal Chemistry Letters (2012) 22:3912-3915.

* cited by examiner

*Primary Examiner* — Sikarl Witherspoon

(57) ABSTRACT

Disclosed is a chalcone composition for treating diabetes and metabolic syndromes. In particular, the chalcone compound bound with 2-halogen in ring A significantly decreases the blood glucose level in the in vitro anti-diabetic effect experiment. In the in vivo animal model, the leading chalcone compound can prevent the progression of diabetes and control the blood glucose level, and there is no significant difference in the gains in body weight. Throughout the seven-week administration, there are no hepatic or renal toxicity observed.

11 Claims, 5 Drawing Sheets

COMPOSITION FOR TREATING DIABETES AND METABOLIC DISEASES AND A PREPARATION METHOD THEREOF

CROSS-REFERENCE TO RELATED APPLICATION AND CLAIM OF PRIORITY

This application is a 35 U.S.C. §371 national stage application of PCT/US2012/049968, which was filed Aug. 8, 2012 and claimed the benefit of TW100128615, filed Aug. 10, 2011, both of which are incorporated herein by reference as if fully set forth.

FIELD OF THE INVENTION

The present invention relates to a chalcone composition. In particular, the present invention relates to a chalcone composition for treating diabetes and metabolic syndromes and the preparation method thereof.

BACKGROUND OF THE INVENTION

Chalcone belongs to a genus of flavonoid compounds. In natural products, chalcone principally exists in plants such as Asteraceae, Lauraceae, Liliaceae and so on.

The basic structure of chalcone is shown as follows.

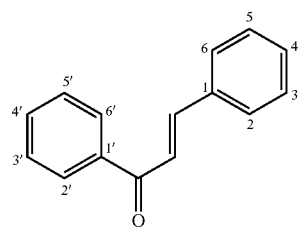 [SMILES: O=C(/C=C/c1ccccc1)c1ccccc1]

Chalcones and their derivatives have been found to have bactericidal, anti-fungal, anti-cancer, and anti-inflammatory activities and so on, and have sugariness and the characteristic of drug. For instance, para-hydroxy (2'-hydroxy or 6'-hydroxy) is the essential substituent for bactericidal activity, 2',4'-dihydroxy 3,4-dihydroxy and 2',4'-dihydroxy 4-hydroxy chalcone derivatives have inhibition activity of aldose reductase and thus can be drugs for reducing or delaying the complications of diabetes (Severi et al., Eur. J. Med. Chem. 1998, 33(11): 859-866); 2,4,5-methoxy 3',6'-dihydroxy chalcone derivative isolated from *Fissistigma lanuginosum* can inhibit tubulins to polymerize as microtubules (Alias et al., J. Nat. Prod. 1995, 58(8): 1160-1166); and 2',3,4-trihydroxy 5'-methyl, and 2',3,4-trimethyl 5'-isopropyl chalcone derivatives have topical anti-inflammatory activity (Sogawa et al., J. Med. Chem. 1993, 36(24): 3904-3909).

The current hypoglycemic medicines include sulfonylurea insulin secretagogues, non-sulfonylurea insulin secretagogues, biguanides, α-glucosidase inhibitors (AGI), thiozidinediones (TZDs, or insulin sensitizers) and dipeptidyl peptidase IV inhibitors (DPP-4 inhibitor). However, they represent side effects with different severity levels. For instance, metformin, a species of biguanides, generates side effects of diarrhea, anorexia, vomit and the most seriously lethal lactic acidosis. Acarbose, a species of AGI, is capable of generating side effect on gastrointestinal tract.

Insulin sensitizers include troglitazone, rosiglitazone (RSZ), pioglitazone (PIO), etc. This types of medicines can enhance the sensitivity of peripheral tissues to insulin, cannot stimulate insulin secretion, intervene to regulate gene transcription of cells via peroxisome proliferator activated receptor gamma (PPARγ) to increase the synthesis of glucose transporter in cells and enhance the glucose usage in cells, and thus decrease the glucose level in the blood. However, the adverse drug reaction of this medicine includes edema, body weight gain, congestive heart failure and the severest hepatotoxicity. Therefore, searching novel anti-hyperglycemic agent without the aforementioned side effects becomes a new issue on new drug development.

It is therefore attempted by the applicant to deal with the above situation encountered in the prior art.

SUMMARY OF THE INVENTION

For developing novel medicine without side effects of the commercial hypoglycemia agents, novel chalcone compositions or compounds, which are effective in promoting the glucose absorption in cells, inhibiting glycemia, curing diabetes and metabolic syndromes, are synthesized in the present invention to have the highly potential value in the new drug market.

The term "derivative" used herein refers to the hydrogen atom or the substituent of a molecule is replaced by other atom or other substituent, and another molecule is generated. The term "compound" used herein refers to two or more types of molecules are chemically boned to form another type of molecule using the specific molar ratio (or weight ratio) under the adequate reaction conditions.

The "compounds" of the invention are afforded in accordance with the preparation method disclosed in the detailed description, the substituent of the specific compounds can be replaced by other substituents, and thus other derivatives can be prepared based on this spirit of the invention. Accordingly, "chalcone compound", "chalcone derivative", "compound" and "derivative" can be alternatively used.

The present invention provides a composition for treating diabetes and/or a metabolic syndrome, including a chalcone compound represented by formula I:

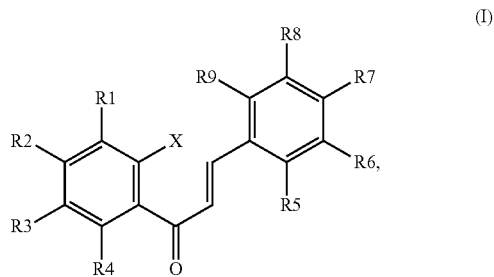

wherein each of X, R1, R2, R3 and R4 is hydrogen (H), hydroxide (—OH) or halogen, and each of R5, R6, R7, R8 and R9 is H, —OH, a $C_1$ to $C_{20}$ alkoxy group or a benzyloxy group.

Preferably, halogen is referred to fluoride (F), chloride (Cl), bromide (Br) or iodine (I). In addition, diabetes or the metabolic syndrome occurs in a subject which might be human beings or rodents. Furthermore, the composition is effective in regulating and/or stabilizing the subject's blood glucose value, alternatively, inhibiting and/or delaying the metabolic syndromes. When the subject is subjected to an impaired glucose tolerance and/or a body weight gain, and the composition is effective in inhibiting the impaired glucose tolerance, the body weight gain, and/or the accumulation of lipid droplets in adipocytes.

The present invention provides a composition for inhibiting body weight gain, including a chalcone compound represented by the above-mentioned formula I, wherein R1 to R9 substituted groups are listed as above.

Preferably, the body weight gain occurs in a subject, which is a mouse. The mouse is continuously fed with a high fat diet (with at least 40 weight % of fat) and is subjected to impaired glucose intolerance. The subject has adipocytes distributed in the tissues of his/her body, and the composition is beneficial in inhibiting the accumulation of lipid droplets in the adipocytes.

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

Figure 1:
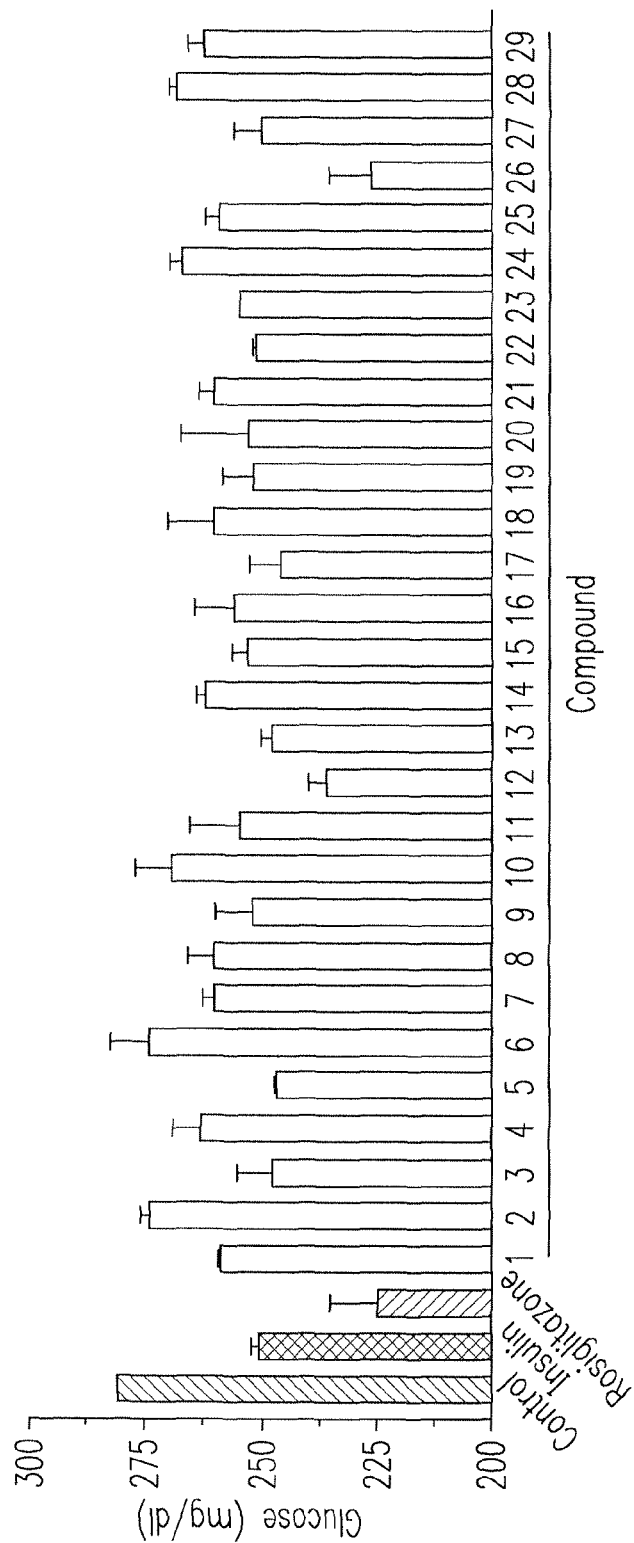
FIG. 1 is a diagram showing the glucose absorption activity of adipocytes 3T3-L1 enhanced by the various chalcone compounds.

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Embodiment

Experiment 1: Preparation of Chalcone Compounds

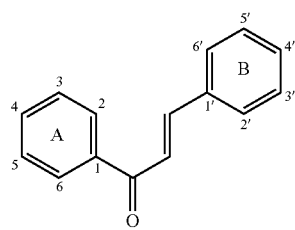

Chalcone compound has ring A and ring B. For ease of illustration, the denotations of carbon atoms in ring A and ring B are shown as above.

The synthesis of the chalcone compounds of the present invention was carried out by a Claisen-Schmidt condensation. Taking chalcone compound 1 as the example, a mixture of 2-hydroxyacetophenone (273.6 mg, 2.01 mmol), 4-methoxybenzaldehyde (279.1 mg, 2.05 mmol), potassium hydroxide (KOH, 50% w/v, 2 ml) and ethanol (100% v/v, 20 ml) was stirred at room temperature for 24 hours. The reaction mixture was concentrated under reduced pressure and then partitioned with ethyl acetate (EtOAc) and $H_2O$. The organic layer was then evaporated, and the residue was purified using column chromatography (silica gel: 70-230, Merck; n-hexane-EtOAc, 15:1, Rf=0.2) to give 2-hydroxy-4'-methoxychalcone (chalcone compound 1, 273.6 mg; yield, 53.6%). The purity of compound 1 was greater than 95%, which was determined by high-performance liquid chromatography (HPLC).

Chalcone compounds 1 to 60 of the present invention prepared based on the aforementioned prepared method are listed as follows. However, chalcone compounds are not limited in the examples of compounds 1 to 60, other chalcone compounds prepared by this method and within the spirit are encompassed in the examples and protecting scope of the present invention.

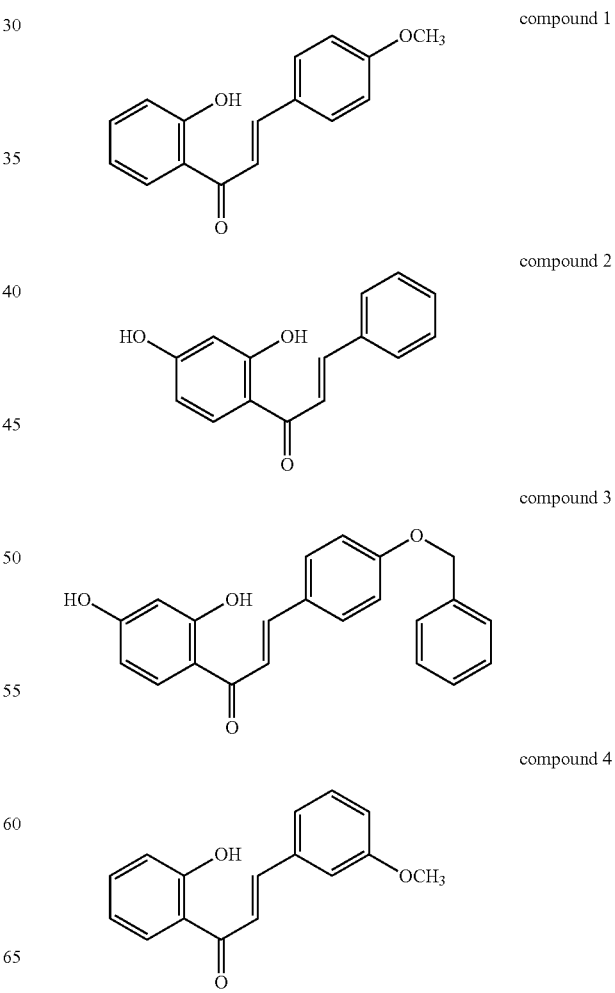

-continued compound 5 compound 6 compound 7 compound 8 compound 9 compound 10 compound 11 compound 12 compound 13 compound 14 compound 15 compound 16 compound 17 compound 18 compound 19
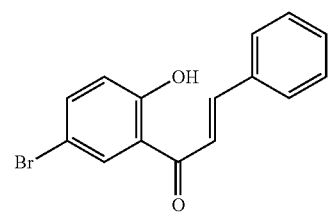
compound 20
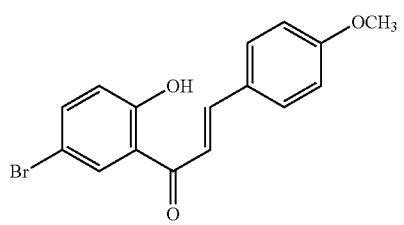
compound 21
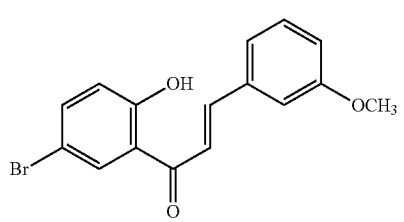
compound 22
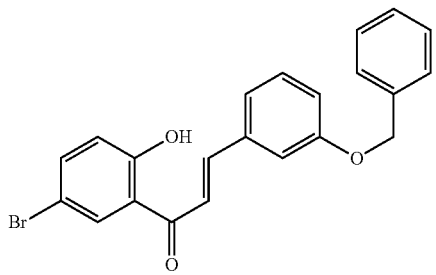
compound 23
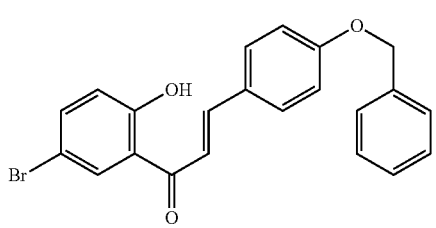
compound 24
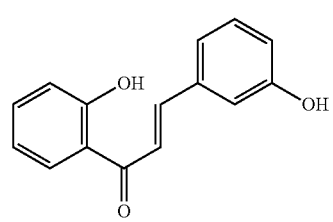
compound 25
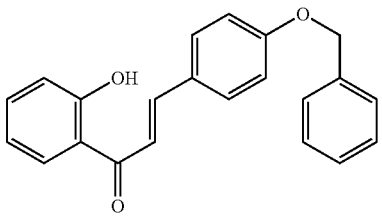
compound 26
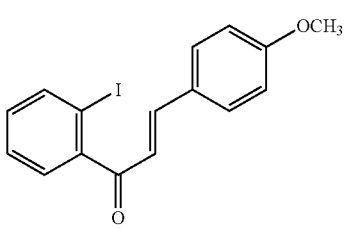
compound 27
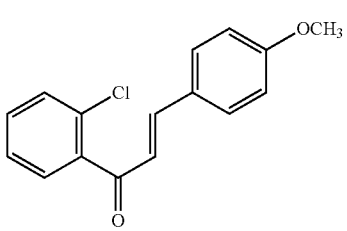
compound 28
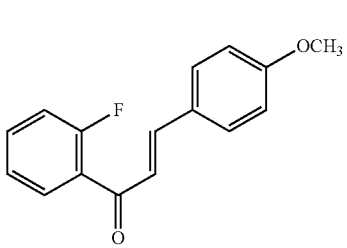
compound 29
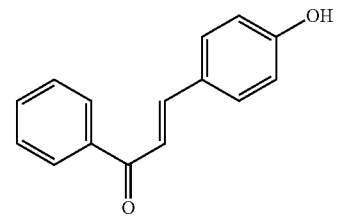
compound 30
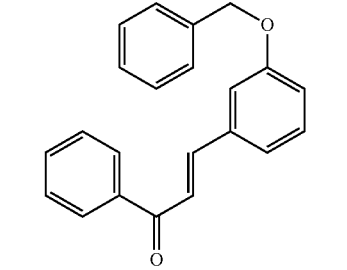

compound 31
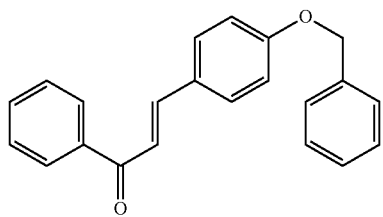
compound 32
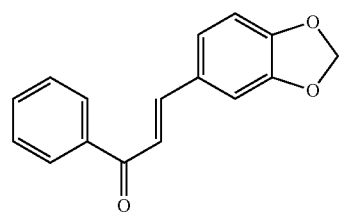
compound 33
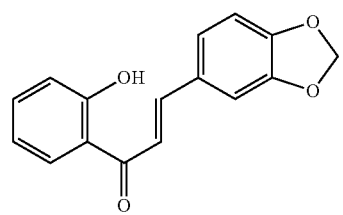
compound 34
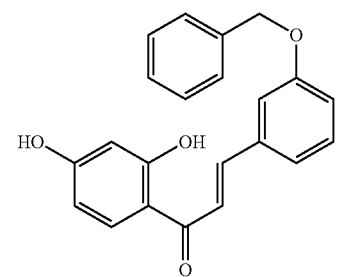
compound 35
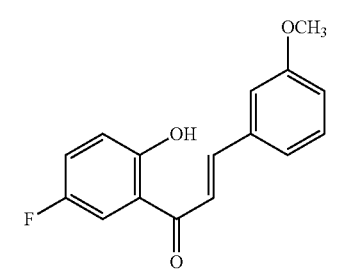
compound 36
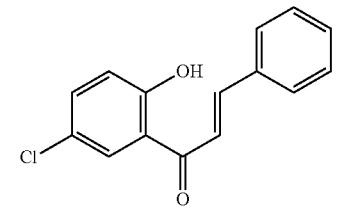
compound 37
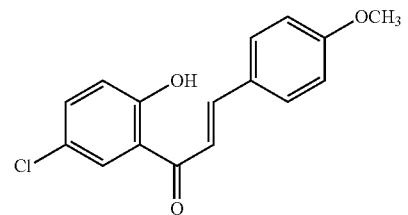
compound 38
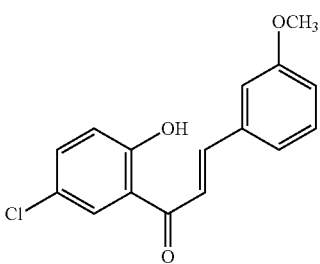
compound 39
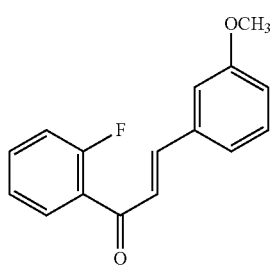
compound 40
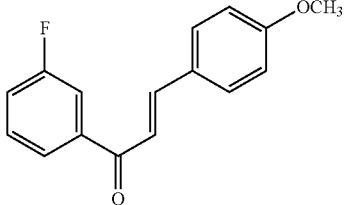
compound 41
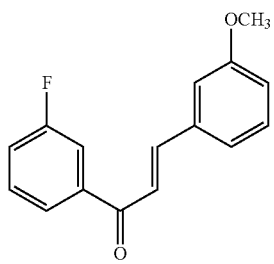
compound 42
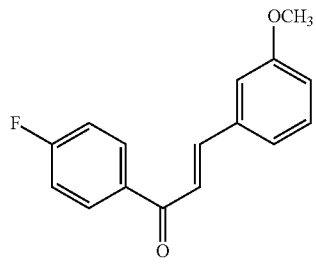
compound 43
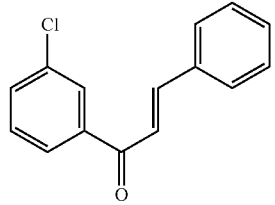

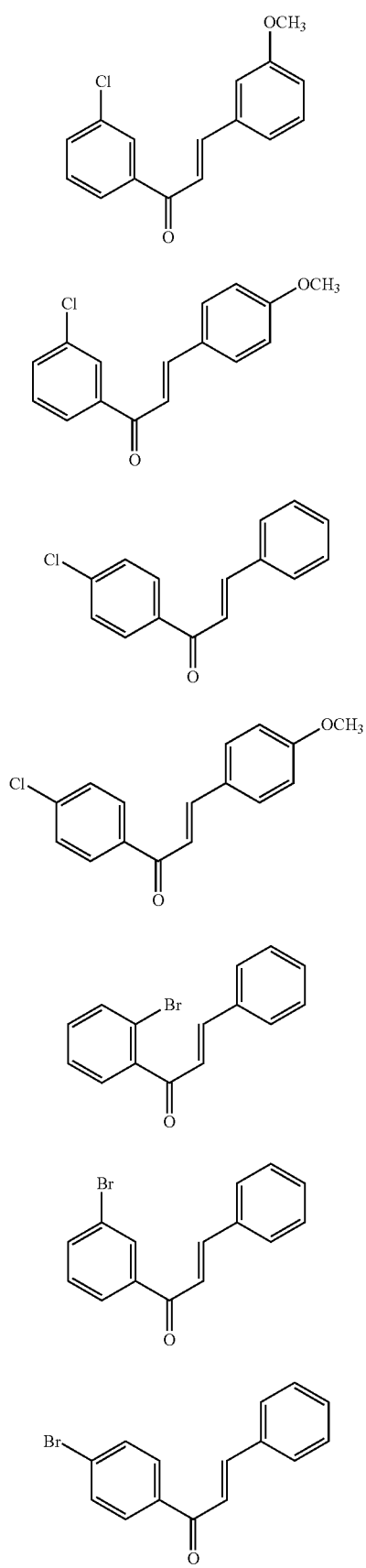
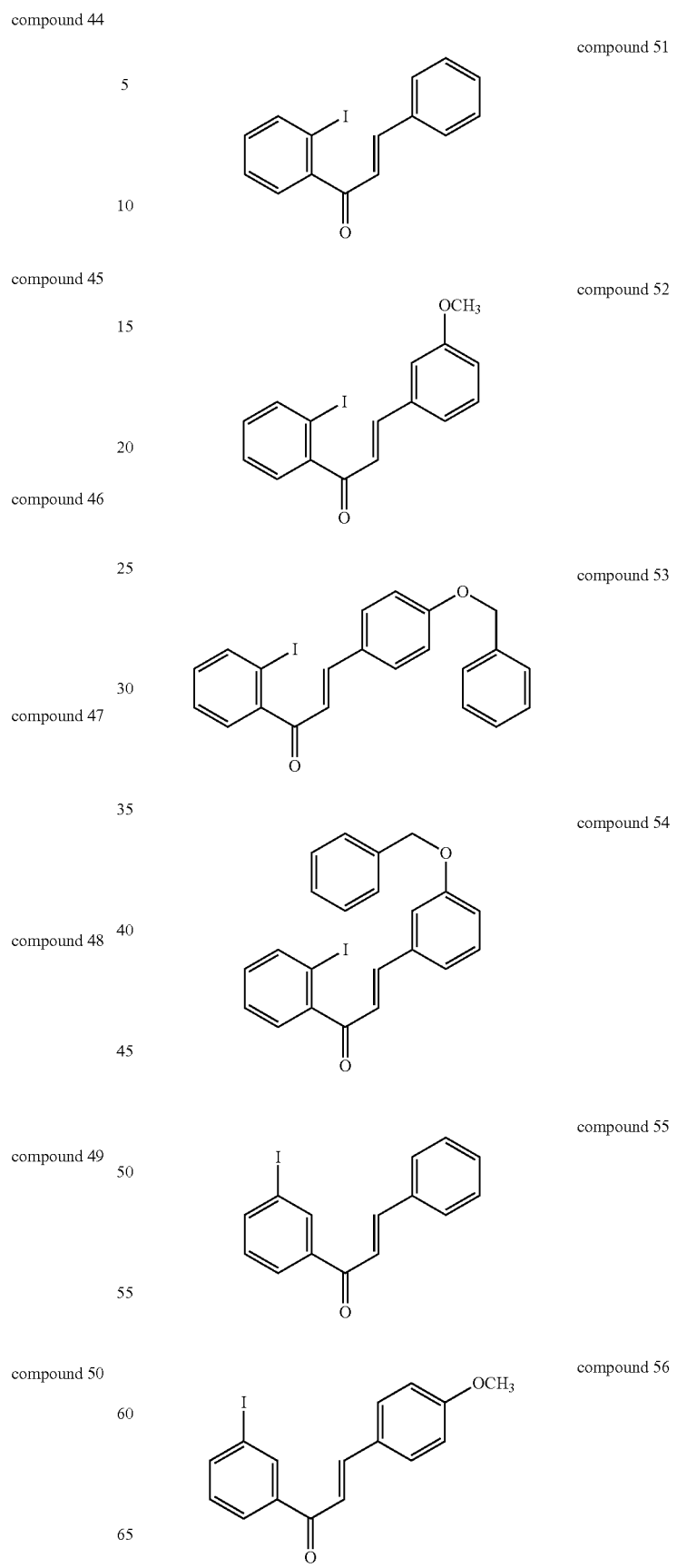

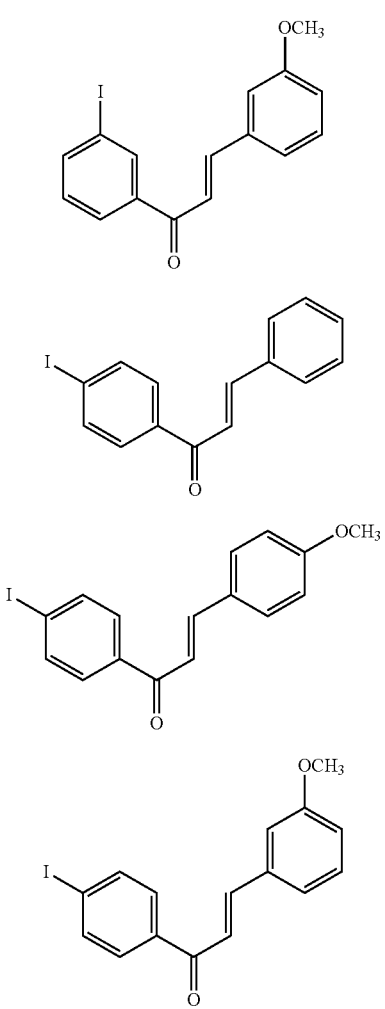

compound 57 compound 58 compound 59 compound 60

Compound 1: ((E)-1-(2-hydroxyphenyl)-3-(4-methoxyphenyl)prop-2-en-1-one).

Compound 2: ((E)-1-(2,4-dihydroxyphenyl)-3-phenylprop-2-en-1-one): $^1$H NMR (400 MHz, Acetone) δ 8.16 (d, J=8.98 Hz, 1H), 7.94 (d, J=15.02 Hz, 1H), 7.86 (d, J=15.20 Hz, 3H), 7.46 (dd, J=1.83, 4.95 Hz, 3H), 6.46-6.58 (m, 1H), 6.39 (s, 1H); $^{13}$C NMR (101 MHz, Acetone) δ 192.8, 167.8, 166.1, 144.8, 136.0, 133.6, 131.5, 129.9, 129.7, 121.8, 114.5, 108.9, 103.7.

Compound 3: ((E)-3-(4-(benzyloxy)phenyl)-1-(2,4-dihydroxyphenyl)prop-2-en-1-one): ESIMS m/z 347.05; $^1$H NMR (400 MHz, Acetone) δ 8.15 (d, J=8.79 Hz, 1H), 7.91-8.03 (m, 1H), 7.77-7.89 (m, 1H), 7.29-7.62 (m, 8H), 7.12 (d, J=7.51 Hz, 1H), 6.49 (d, J=8.98 Hz, 1H), 6.39 (d, J=0.73 Hz, 1H), 5.20 (s, 2H); $^{13}$C NMR (101 MHz, Acetone) δ 191.7, 167.9, 166.1, 160.2, 144.7, 138.5, 137.3, 133.6, 130.9, 129.4, 129.3, 128.9, 128.7, 122.9, 121.9, 119.6, 118.3, 115.4, 114.5, 109.1, 103.7, 70.7.

Compound 4: ((E)-1-(2-hydroxyphenyl)-3-(3-methoxyphenyl)prop-2-en-1-one).

Compound 5: ((E)-1-(2,4-dihydroxyphenyl)-3-(4-methoxyphenyl)-prop-2-en-1-one): ESIMS m/z 271.03; $^1$H NMR (400 MHz, Acetone) δ 8.13 (d, J=8.79 Hz, 1H), 7.82 (dt, J=8.80, 15.40 Hz, 4H), 7.01 (d, J=8.61 Hz, 2H), 6.48 (dd, J=2.20, 8.79 Hz, 1H), 6.34 (d, J=2.20 Hz, 1H), 3.86 (s, 3H); $^{13}$C NMR (101 MHz, Acetone) δ 192.8, 167.7, 165.8, 162.9, 144.8, 133.4, 131.6, 128.6, 119.1, 115.3, 114.5, 108.8, 103.8, 55.9.

Compound 6: ((E)-1-(2,4-dihydroxyphenyl)-3-(3-methoxyphenyl)-prop-2-en-1-one): ESIMS m/z 270.97; $^1$H NMR (400 MHz, Acetone) δ 8.16 (d, J=8.79 Hz, 1H), 7.96 (d, J=15.57 Hz, 1H), 7.83 (d, J=15.39 Hz, 1H), 7.40-7.46 (m, 2H), 7.36 (t, J=7.69 Hz, 1H), 7.03 (d, J=7.14 Hz, 1H), 6.50 (dd, J=2.20, 8.98 Hz, 1H), 6.34 (d, J=2.20 Hz, 1H), 3.87 (s, 3H).

Compound 7: (E)-3-(4-methoxyphenyl)-1-phenylprop-2-en-1-one.

Compound 8: ((E)-3-(3-methoxyphenyl)-1-phenylprop-2-en-1-one): ESIMS m/z 239.02; $^1$H NMR (400 MHz, Acetone) δ 8.17 (d, J=8.79 Hz, 2H), 7.88 (d, J=15.75 Hz, 1H), 7.76 (d, J=15.75 Hz, 1H), 7.60 (d, J=8.61 Hz, 2H), 7.39 (t, J=7.51 Hz, 4H), 7.03 (td, J=2.20, 7.33 Hz, 1H), 3.86 (s, 3H); $^{13}$C NMR (101 MHz, Acetone) δ188.9, 161.2, 145.5, 139.5, 137.7, 137.3, 131.2, 130.9, 129.8, 122.8, 122.3, 117.5, 114.3, 55.8.

Compound 9: (E)-chalcone.

Compound 10: ((E)-3-(benzo[d][1,3]dioxol-5-yl)-1-phenylprop-2-en-1-one): ESIMS m/z 225.04; $^1$H NMR (400 MHz, Acetone) δ 8.29 (d, J=7.14 Hz, 1H), 8.05 (d, J=15.39 Hz, 1H), 7.95 (t, J=15.94 Hz, 1H), 7.84-7.91 (m, 2H), 7.54-7.64 (m, 1H), 7.42-7.52 (m, 3H), 6.99 (d, J=7.88 Hz, 2H); $^{13}$C NMR (101 MHz, Acetone) δ 195.1, 164.6, 146.3, 137.5, 135.7, 131.9, 131.5, 130.0, 129.9, 121.5, 120.9, 119.9, 119.0.

Compound 11: ((E)-3-(3-(benzyloxy)phenyl)-1-(2-hydroxyphenyl)prop-2-en-1-one): ESIMS m/z 331.07; $^1$H NMR (400 MHz, Acetone) δ 8.26 (dd, J=1.28, 8.24 Hz, 1H), 7.86 (d, J=8.79 Hz, 4H), 7.55 (t, J=8.10 Hz, 1H), 7.50 (d, J=7.33 Hz, 2H), 7.41 (t, J=7.33 Hz, 2H), 7.31-7.38 (m, 1H), 7.12 (d, J=8.61 Hz, 2H), 6.93-7.04 (m, 2H), 5.21 (s, 2H); $^{13}$C NMR (101 MHz, Acetone) δ 194.2, 163.5, 160.3, 147.2, 140.0, 138.1, 137.0, 133.4, 131.0, 129.4, 128.8, 128.7, 123.4, 122.3, 121.4, 121.3, 118.9, 115.6, 111.1, 70.7.

Compound 12: ((E)-1-(2-bromophenyl)-3-(4-methoxyphenyl)prop-2-en-1-one): EIMS m/z 316.89; $^1$H NMR (400 MHz, Acetone) δ 7.71 (dd, J=8, 0.8 Hz, 1H), 7.60 (d, J=7.3 Hz, 2H), 7.41-7.53 (m, 3H), 7.74 (d, J=16.5 Hz, 1H), 7.03 (d, J=16.5 Hz, 1H), 6.799 (d, J=7.3 Hz, 2H), 3.85 (s, 3H); $^{13}$C NMR (101 MHz, Acetone) δ 194.6, 163.1, 147.2, 142.7, 134.1, 132.2, 131.5, 130.0, 128.5, 128.1, 124.8, 119.7, 115.4, 55.9.

Compound 13: ((E)-1-(2-bromophenyl)-3-(3-methoxyphenyl)prop-2-en-1-one): ESIMS m/z 318.95; $^1$H NMR (400 MHz, Acetone) δ 7.72 (d, J=7.88 Hz, 1H), 7.49-7.57 (m, 2H), 7.42-7.47 (m, 1H), 7.41 (d, J=16.12 Hz, 1H), 7.35 (t, J=7.69 Hz, 1H), 7.25-7.32 (m, 2H), 7.19 (d, J=16.12 Hz, 1H), 7.02 (dd, J=1.92, 8.15 Hz, 1H), 3.83 (s, 3H); $^{13}$C NMR (101 MHz, Acetone) δ 194.6, 161.5, 147.1, 142.4, 136.8, 134.2, 132.4, 130.9, 130.0, 128.6, 127.3, 122.2, 119.7, 118.0, 114.0, 55.8.

Compound 14: ((E)-1-(3-bromophenyl)-3-(3-methoxyphenyl)prop-2-en-1-one): ESIMS m/z 316.95; HRESIMS: calcd for $C_{16}H_{13}BrO_2Na$: 338.9997. found: m/z 338.9995, 340.9976; $^1$H NMR (400 MHz, Acetone) δ 8.27 (t, J=1.74 Hz, 1H), 8.15 (d, J=7.88 Hz, 1H), 7.89 (d, J=15.75 Hz, 1H), 7.83 (d, J=0.92 Hz, 1H), 7.79 (d, J=15.39 Hz, 1H), 7.53 (t, J=7.88 Hz, 1H), 7.42-7.47 (m, 1H), 7.41 (s, 1H), 7.37 (t, J=8.06 Hz, 1H), 7.04 (qd, J=1.30, 8.06 Hz, 1H), 3.74-4.05 (m, 3H); $^{13}$C NMR (101 MHz, Acetone) δ 188.7, 161.2, 145.8, 141.1, 137.3, 136.5, 132.1, 131.7, 130.9, 128.3, 123.4, 122.6, 122.5, 117.7, 114.3, 55.8.

Compound 15: ((E)-1-(4-chlorophenyl)-3-(3-methoxyphenyl)prop-2-en-1-one): ESIMS m/z 273.02; $^1$H NMR (400 MHz, Acetone) δ 8.16 (d, J=8.24 Hz, 2H), 7.87 (d, J=15.57 Hz, 1H), 7.76 (d, J=15.57 Hz, 1H), 7.59 (d, J=8.43 Hz, 2H), 7.39 (dtd, J=2.02, 7.51, 9.71 Hz, 3H), 7.03 (td, J=2.20, 7.14 Hz, 1H), 3.86 (s, 3H); $^{13}$C NMR (101 MHz, Acetone) δ 188.9, 161.2, 145.5, 139.5, 137.7, 137.3, 131.2, 130.9, 129.8, 122.8, 122.3, 117.5, 114.3, 55.8.

Compound 16: ((E)-1-(4-bromophenyl)-3-(3-methoxyphenyl)prop-2-en-1-one): EIMS m/z 316.00; $^1$H NMR (200 MHz, Acetone) δ 8.8 (d, J=8.6 Hz, 2H), 7.89 (d, J=15.8 Hz, 1H), 7.82-7.79 (m, 1H), 7.74 (d, J=8.6 Hz, 2H), 7.74-7.35 (m, 2H), 7.36 (d, J=15.8 Hz, 1H), 7.06-6.99 (m, 1H), 3.86 (s, 3H); $^{13}$C NMR (50 MHz, Acetone) δ 188.7, 160.7, 145.1, 137.6, 136.9, 132.4, 130.9, 130.5, 127.8, 122.3, 121.9, 117.1, 113.9, 55.4.

Compound 17: ((E)-1-(3-bromophenyl)-3-(4-methoxyphenyl)prop-2-en-1-one): ESIMS m/z 316.90, 318.89; $^1$H NMR (400 MHz, Acetone) δ 8.25 (t, J=1.74 Hz, 1H), 8.13 (d, J=7.88 Hz, 1H), 7.81 (dd, J=8.61, 16.85 Hz, 4H), 7.74 (dd, J=1.00, 16.49 Hz, 1H), 7.52 (t, J=7.88 Hz, 1H), 7.02 (d, J=8.79 Hz, 2H), 3.63-4.08 (m, 3H); $^{13}$C NMR (101 MHz, Acetone) δ 188.5, 163.0, 145.8, 141.5, 136.3, 132.0, 131.7, 131.6, 130.3, 128.5, 128.1, 123.4, 119.9, 115.3, 55.9.

Compound 18: ((E)-1-(4-bromophenyl)-3-(4-methoxyphenyl)prop-2-en-1-one): ESIMS m/z 316.90, 318.89; $^1$H NMR (400 MHz, CHLOROFORM-d) δ 7.91 (d, J=8.79 Hz, 2H), 7.78 (d, J=15.57 Hz, 1H), 7.63 (d, J=8.43 Hz, 2H), 7.59 (d, J=8.79 Hz, 2H), 7.36 (d, J=15.57 Hz, 1H), 6.94 (d, J=8.61 Hz, 2H), 3.86 (s, 3H); $^{13}$C NMR (101 MHz, CHLOROFORM-d) δ 189.3, 161.8, 145.2, 137.1, 131.8, 130.3, 129.9, 127.6, 127.3, 119.0, 114.4, 55.4.

Compound 19: ((E)-1-(5-bromo-2-hydroxyphenyl)-3-phenylprop-2-en-1-one): ESIMS m/z 302.9, 304.9; $^1$H NMR (200 MHz, CDCl$_3$) δ 8.41 (d, J=2.6 Hz, 1H), 8.1 (d, J=15.4 Hz, 1H), 7.94 (d, J=15.4 Hz, 1H), 7.90 (m, 1H), 7.67 (dd, J=2.2, 9.0 Hz, 1H), 7.50 (d, J=2.80 Hz, 2H), 7.47 (m, 1H), 6.95 (d, J=9 Hz, 1H); $^{13}$C NMR (50 MHz, CDCl$_3$) δ 194.8, 164.1, 147.3, 140.5, 136.2, 134.0, 132.7, 130.8, 130.5, 122.9, 121.8, 121.7, 111.7.

Compound 20: ((E)-1-(5-bromo-2-hydroxyphenyl)-3-(4-methoxyphenyl)prop-2-en-1-one): ESIMS m/z 332.93, 334.92; $^1$H NMR (400 MHz, Acetone) δ 8.40 (d, J=2.38 Hz, 1H), 7.95 (t, J=15.00 Hz, 2H), 7.85 (d, J=8.79 Hz, 2H), 7.66 (dd, J=2.02, 8.79 Hz, 1H), 7.04 (d, J=8.98 Hz, 2H), 6.94 (d, J=9.34 Hz, 1H), 3.87 (s, 3H); $^{13}$C NMR (101 MHz, Acetone) δ 194.1, 163.0, 147.4, 139.7, 133.2, 132.3, 128.2, 122.4, 121.2, 118.4, 115.4, 111.0, 55.9.

Compound 21: ((E)-1-(5-bromo-2-hydroxyphenyl)-3-(3-methoxyphenyl)prop-2-en-1-one): ESIMS m/z 332.9, 334.9; $^1$H NMR (400 MHz, Acetone) δ 8.41 (d, J=2.20 Hz, 1H), 8.11 (d, J=15.20 Hz, 1H), 7.94 (d, J=15.39 Hz, 1H), 7.69 (dd, J=2.38, 8.98 Hz, 1H), 7.44-7.55 (m, 2H), 7.39 (t, J=7.70 Hz, 1H), 7.07 (dd, J=2.01, 8.24 Hz, 1H), 6.95 (d, J=8.98 Hz, 1H), 3.86 (s, 3H); $^{13}$C NMR (101 MHz, Acetone) δ 194.3, 163.5, 161.2, 147.3, 139.9, 136.9, 133.2, 130.9, 123.0, 122.3, 121.3, 118.2, 114.6, 111.1, 55.7.

Compound 22: ((E)-3-(3-(benzyloxy)phenyl)-1-(5-bromo-2-hydroxyphenyl)prop-2-en-1-one): ESIMS m/z 408.89, 410.94; $^1$H NMR (400 MHz, Acetone) δ 8.40 (d, J=2.38 Hz, 1H), 8.08 (d, J=15.57 Hz, 1H), 7.95 (d, J=15.39 Hz, 1H), 7.69 (dd, J=2.38, 8.79 Hz, 1H), 7.60 (t, J=2.00 Hz, 1H), 7.52 (d, J=7.33 Hz, 2H), 7.47 (d, J=7.69 Hz, 1H), 7.42 (td, J=7.30, 8.06 Hz, 2H), 7.30-7.38 (m, 2H), 7.15 (dd, J=2.01, 8.06 Hz, 1H), 6.95 (d, J=8.98 Hz, 1H), 5.18 (s, 2H); $^{13}$C NMR (101 MHz, Acetone) δ 194.2, 163.5, 160.3, 147.2, 140.0, 138.1, 137.0, 133.4, 131.0, 129.4, 128.8, 128.7, 123.4, 122.3, 121.4, 121.3, 118.9, 115.6, 111.1, 70.7.

Compound 23: ((E)-3-(4-(benzyloxy)phenyl)-1-(5-bromo-2-hydroxyphenyl)prop-2-en-1-one): ESIMS m/z 408.95, 410.94; $^1$H NMR (400 MHz, Acetone) δ 8.41 (d, J=2.38 Hz, 1H), 8.00 (t, J=15.40 Hz, 2H), 7.85 (d, J=8.61 Hz, 2H), 7.68 (dd, J=2.38, 8.98 Hz, 1H), 7.46-7.55 (m, 2H), 7.42 (t, J=7.14 Hz, 2H), 7.28-7.37 (m, 1H), 7.13 (d, J=8.79 Hz, 2H), 6.94 (d, J=8.43 Hz, 1H), 5.18-5.27 (m, 2H); $^{13}$C NMR (101 MHz, Acetone) δ 193.4, 168.3, 166.7, 145.4, 136.6, 135.0, 134.2, 132.0, 130.4, 130.3, 122.3, 115.1, 109.6, 109.4, 104.4, 104.1.

Compound 24: (2E)-1-(2-hydroxyphenyl)-3-(4-hydroxyphenyl)-2-propen-1-one.

Compound 25: ((E)-3-(4-(benzyloxy)phenyl)-1-(2-hydroxyphenyl)prop-2-en-1-one): ESIMS m/z 331.01; $^1$H NMR (400 MHz, Acetone) δ 8.27 (dd, J=1.10, 8.24 Hz, 1H), 7.93 (t, J=15.00 Hz, 2H), 7.83 (d, J=8.79 Hz, 2H), 7.56 (t, J=6.80 Hz, 1H), 7.49 (d, J=7.14 Hz, 2H), 7.41 (t, J=7.10 Hz, 2H), 7.34 (d, J=7.14 Hz, 1H), 7.14 (d, J=8.98 Hz, 2H), 6.98 (td, J=6.80, 8.24 Hz, 2H), 5.21 (s, 2H); $^{13}$C NMR (101 MHz, Acetone) δ 194.9, 164.6, 162.3, 146.3, 137.9, 137.2, 131.9, 131.3, 129.4, 128.9, 128.6, 121.0, 119.8, 119.0, 118.9, 116.3, 70.7.

Compound 26: ((E)-1-(2-iodophenyl)-3-(4-methoxyphenyl)prop-2-en-1-one): ESIMS m/z 364.99; HRESIMS: calcd for C$_{16}$H$_{13}$IO$_2$: 365.0039. found: m/z 365.0040; $^1$H NMR (400 MHz, Acetone) δ 7.98 (d, J=7.88 Hz, 1H), 7.69 (d, J=8.79 Hz, 2H), 7.55 (dt, J=0.92, 7.51 Hz, 1H), 7.45 (dd, J=1.47, 7.51 Hz, 1H), 7.37 (d, J=16.12 Hz, 1H), 7.26 (dt, J=1.56, 7.65 Hz, 1H), 7.02 (d, J=16.12 Hz, 1H), 7.02 (d, J=8.79 Hz, 2H), 3.86 (s, 3H); $^{13}$C NMR (101 MHz, Acetone) δ 196.1, 163.1, 147.4, 146.3, 140.8, 132.1, 131.5, 129.3, 129.1, 128.1, 124.3, 115.4, 92.6, 55.9.

Compound 27: ((E)-1-(2-chlorophenyl)-3-(4-methoxyphenyl)prop-2-en-1-one): ESIMS m/z 272.95; $^1$H NMR (400 MHz, Acetone) δ 7.682 (d, J=7.2 Hz, 2H), 7.51-7.54 (m, 2H), 7.45-7.49 (m, 1H), 7.408 (d, J=12.8 Hz, 1H), 7.061 (d, J=12.8 Hz, 1H), 7.001 (d, J=7.2 Hz, 2H), 3.86 (s, 3H); $^{13}$C NMR (101 MHz, Acetone) δ 193.8, 163.1, 147.0, 140.6, 132.2, 131.5, 131.4, 130.9, 130.1, 128.1, 125.0, 115.4, 55.9.

Compound 28: ((E)-1-(2-fluorophenyl)-3-(4-methoxyphenyl)prop-2-en-1-one): ESIMS m/z 257.07; $^1$H NMR (400 MHz, Acetone) δ 7.77 (td, J=6, 0.8 Hz, 1H), 7.72 (d, J=6.8 Hz, 2H), 7.66 (d, J=12.4 Hz, 1H), 7.60-7.65 (m, 1H), 7.34 (td, J=6, 0.8 Hz, 1H), 7.27 (d, J=12.4 Hz, 1H), 7.26-7.30 (m, 1H), 7.01 (d, J=6.8 Hz, 2H), 3.86 (s, 3H); $^{13}$C NMR (101 MHz, Acetone) δ 189.3 (d, J=6.6), 163.0, 161.7 (d, J=199), 145.4, 134.6 (d J=6.6), 131.5 (d, J=2.2), 131.4, 128.6 (d J=10), 128.3, 125.5 (d, J=3), 124.3 (d, J=4.4), 117.3 (d, J=18.3), 115.4, 55.9.

Compound 29: (E)-3-(4-hydroxyphenyl)-1-phenylprop-2-en-1-one.

Compound 30: ((E)-3-(3-(benzyloxy)phenyl)-1-phenylprop-2-en-1-one): ESIMS m/z 314.95; $^1$H NMR (400 MHz, Acetone) δ 8.14 (d, J=7.2 Hz, 2H), 7.88 (d, J=16 Hz, 1H), 7.76 (d, J=16 Hz, 1H), 7.65 (t, J=7.2 Hz, 1H), 7.51-7.58 (m, 5H), 7.32-7.43 (m, 5H), 7.11 (d, J=7.6 Hz, 1H), 5.21 (s, 2H); $^{13}$C NMR (101 MHz, Acetone) δ 191.5, 160.9, 145.1, 139.7, 134.4, 131.5, 130.2, 129.9, 129.4, 129.3, 123.8, 123.2, 118.8, 115.7, 115.7, 111.9, 71.2.

Compound 31: ((E)-3-(4-(benzyloxy)phenyl)-1-phenylprop-2-en-1-one): ESIMS m/z 314.95; $^1$H NMR (400 MHz, Acetone) δ 8.13 (d, J=8 Hz, 2H), 7.82 (d, J=9.6 Hz, 2H), 7.75 (d, J=15.6 Hz, 1H), 7.73 (d, J=15.6 Hz, 1H), 7.64 (t, J=5.2 Hz, 1H), 7.49-7.57 (m, 4H), 7.41 (d, J=8.4 Hz, 2H), 7.326-7.365 (m, 1H), 7.11 (d, J=8.8 Hz, 2H), 5.213 (s, 2H); $^{13}$C NMR (101 MHz, Acetone) δ 190.5, 162.2, 145.4, 135.5, 134.1, 132.0, 130.1, 130.0, 129.9, 129.5, 129.2, 127.5, 123.3, 121.2, 116.8, 71.2.

Compound 32: (E)-3-(benzo[d][1,3]dioxol-5-yl)-1-phenylprop-2-en-1-one.

Compound 33: (E)-3-(benzo[d][1,3]dioxol-5-yl)-1-(2-hydroxyphenyl)prop-2-en-1-one.

Compound 34: ((E)-3-(3-(benzyloxy)phenyl)-1-(2,4-dihydroxyphenyl)prop-2-en-1-one): ESIMS m/z 346.99; 1H NMR (400 MHz, Acetone) δ 8.12 (d, J=9.2 Hz, 1H), 7.95 (d, J=15.6 Hz, 1H), 7.82 (d, J=15.6 Hz, 1H), 7.50-7.55 (m, 3H), 7.32-7.44 (m, 5H), 7.10-7.13 (m, 1H), 6.5 (dd, J=8.9, 2.20 Hz, 1H), 6.4 (d, J=2.20 Hz, 1H); $^{13}$C NMR (101 MHz, Acetone) δ 193.1, 167.6, 160.9, 160.3, 145.1, 138.8, 138.1, 134.2, 131.5, 129.9, 129.4, 129.3, 123.4, 122.8, 118.8, 115.8, 114.7, 109.9, 109.9, 104.5, 70.1.

Compound 35: ((E)-1-(5-fluoro-2-hydroxyphenyl)-3-(3-methoxyphenyl)prop-2-en-1-one): EIMS m/z 272; HREIMS: calcd for $C_{16}H_{13}O_3F$: 272.0839. found: m/z 272.0849; $^1$H NMR (400 MHz, Acetone) δ 8.06 (dd, J=3.66, 9.34 Hz, 1H), 8.03 (d, J=15.75 Hz, 1H), 7.94 (d, J=15.39 Hz, 1H), 7.51 (s, 5H), 7.04-7.12 (m, 1H), 6.91-7.04 (m, 1H), 3.87 (s, 3H); $^{13}$C NMR (101 MHz, Acetone) δ 193.6 (d, J=153), 161.0 (d, J=39), 155.9 (d, J=234), 147.1, 139.2, 137.0, 131.0 (d, J=20), 124.8 (d, J=23), 122.6 (d, J=174), 122.2 (d, J=151), 120.4, 118.1, 116.3 (d, J=23), 114.6, 113.6, 56.

Compound 36: ((E)-1-(5-chloro-2-hydroxyphenyl)-3-phenylprop-2-en-1-one): ESIMS m/z 259.04; $^1$H NMR (400 MHz, Acetone) δ 8.30 (d, J=2.56 Hz, 1H), 8.10 (d, J=15.39 Hz, 1H), 7.98 (d, J=15.39 Hz, 1H), 7.84-7.94 (m, 2H), 7.58 (dd, J=2.56, 8.79 Hz, 1H), 7.49 (d, J=2.02 Hz, 3H), 7.04 (d, J=8.79 Hz, 1H); $^{13}$C NMR (101 MHz, Acetone) δ 194.3, 163.1, 147.2, 137.4, 135.6, 132.1, 130.5, 130.2, 129.9, 124.2, 121.7, 121.2, 120.9.

Compound 37: ((E)-1-(5-chloro-2-hydroxyphenyl)-3-(4-methoxyphenyl)prop-2-en-1-one): ESIMS m/z 289.06; $^1$H NMR (400 MHz, Acetone) δ 8.29 (d, J=2.56 Hz, 1H), 7.97 (t, J=15.80 Hz, 2H), 7.89 (d, J=8.61 Hz, 2H), 7.55 (dd, J=2.38, 8.79 Hz, 1H), 7.03 (t, J=8.80 Hz, 3H), 3.88 (s, 3H); $^{13}$C NMR (101 MHz, Acetone) δ 194.2, 163.5, 163.1, 147.4, 136.9, 132.3, 130.3, 128.3, 124.1, 121.8, 120.9, 118.4, 115.4, 56.0.

Compound 38: ((E)-1-(5-chloro-2-hydroxyphenyl)-3-(3-methoxyphenyl)prop-2-en-1-one): $^1$H NMR (400 MHz, Acetone) δ 8.41 (d, J=2.20 Hz, 1H), 8.11 (d, J=15.20 Hz, 1H), 7.94 (d, J=15.39 Hz, 1H), 7.69 (dd, J=2.38, 8.98 Hz, 1H), 7.44-7.55 (m, 2H), 7.39 (t, J=7.70 Hz, 1H), 7.07 (dd, J=2.01, 8.24 Hz, 1H), 6.95 (d, J=8.98 Hz, 1H), 3.86 (s, 3H); $^{13}$C NMR (101 MHz, Acetone) δ 194.3, 163.5, 161.2, 147.3, 139.9, 136.9, 133.2, 130.9, 123.0, 122.3, 121.3, 118.2, 114.6, 111.1, 55.7.

Compound 39: ((E)-1-(2-fluorophenyl)-3-(3-methoxyphenyl)prop-2-en-1-one): EIMS m/z 256; $^1$H NMR (400 MHz, Acetone) δ 7.79 (dt, J=1.83, 7.51 Hz, 1H), 7.59-7.71 (m, 2H), 7.45 (dd, J=2.47, 15.85 Hz, 1H), 7.24-7.40 (m, 5H), 6.99-7.07 (m, 1H), 3.86 (s, 3H); $^{13}$C NMR (101 MHz, Acetone) δ 190.1, 162.4 (d, J=250), 161.8, 146.9, 137.7, 135.4 (d, J=8.3), 132.1 (d, J=9.2), 131.5, 128.9 (d, J=14.4), 127.5 (d, J=4.5), 126.2 (d, J=3), 122.7, 118.3, 118.9 (d, J=22.8), 114.8, 56.3.

Compound 40: ((E)-1-(3-fluorophenyl)-3-(4-methoxyphenyl)prop-2-en-1-one): EIMS m/z 256; HREIMS: calcd for $C_{16}H_{13}O_2F$: 256.0881. found: m/z 256.0901; $^1$H NMR (400 MHz, Acetone) δ 7.98 (d, J=7.69 Hz, 1H), 7.85 (s, 1H), 7.81 (dd, J=8.24, 15.57 Hz, 3H), 7.73 (d, J=15.75 Hz, 1H), 7.60 (dt, J=5.86, 7.88 Hz, 1H), 7.35-7.47 (m, 1H), 7.02 (d, J=8.61 Hz, 2H), 3.87 (s, 3H); $^{13}$C NMR (101 MHz, Acetone) δ 188.6, 163.9 (d, J=244), 163.0, 145.7, 141.8, 141.7 (d, J=5.3), 132.6, 131.6 (d, J=3), 128.5, 125.3, 125.3, 120.1 (d, J=21.8), 115.8 (d, J=22.6), 115.2, 55.9.

Compound 41: ((E)-1-(3-fluorophenyl)-3-(3-methoxyphenyl)prop-2-en-1-one): ESIMS m/z 257.13; HREIMS: calcd for $C_{16}H_{13}O_2F$: 256.0908. found: m/z 256.0898; $^1$H NMR (400 MHz, Acetone) δ 8.01 (d, J=7.69 Hz, 1H), 7.86 (tdd, J=1.28, 8.98, 15.57 Hz, 2H), 7.77 (d, J=15.57 Hz, 1H), 7.63 (dddd, J=2.20, 5.86, 10.08, 21.62 Hz, 1H), 7.40-7.49 (m, 3H), 7.36 (t, J=7.69 Hz, 1H), 7.04 (ddd, J=0.90, 3.48, 7.69 Hz, 1H), 3.87 (s, 3H); $^{13}$C NMR (101 MHz, Acetone) δ 188.8, 163.9 (d, J=244), 161.2, 145.7, 141.4, 137.3, 131.7 (d, J=7.6), 130.9, 125.4 (d, J=3), 122.6 (d, J=3), 120.6 (d, J=21.76), 117.6, 115.8 (d, J=22.7), 114.3, 55.8.

Compound 42: ((E)-1-(4-fluorophenyl)-3-(3-methoxyphenyl)prop-2-en-1-one): ESIMS m/z 257.07; HREIMS: calcd for $C_{16}H_{13}FO_2$: 256.0900. found: m/z 256.0900; $^1$H NMR (400 MHz, Acetone) δ 8.12-8.42 (m, 2H), 7.84-8.03 (m, 1H), 7.70-7.82 (m, 1H), 7.36-7.58 (m, 3H), 7.31 (t, J=8.79 Hz, 2H), 7.03 (td, J=2.18, 7.19 Hz, 1H), 3.87 (s, 3H); $^{13}$C NMR (101 MHz, Acetone) δ 188.5, 166 (d, J=250), 161.2, 145.1, 137.4, 132.3 (d, J=9), 130.9, 123.5, 122.6 (d, J=56), 121, 117.5, 116.6 (d, J=21), 115.2, 114.2, 113.6, 55.8.

Compound 43: ((E)-1-(3-chlorophenyl)-3-phenylprop-2-en-1-one): ESIMS m/z 243.06; $^1$H NMR (400 MHz, CHLOROFORM-d) δ 7.99 (s, 1H), 7.87-7.95 (m, 1H), 7.82 (s, 1H), 7.62-7.72 (m, 2H), 7.53-7.60 (m, 1H), 7.46 (tdd, J=3.11, 7.69, 15.75 Hz, 5H); $^{13}$C NMR (101 MHz, CHLOROFORM-d) δ 189.1, 145.6, 139.7, 134.9, 134.5, 132.7, 130.8, 129.9, 129.0, 128.5, 126.5, 121.4.

Compound 44: ((E)-1-(3-chlorophenyl)-3-(3-methoxyphenyl)prop-2-en-1-one): ESIMS m/z 273.11; HREIMS: calcd for $C_{16}H_{13}O_2Cl$: 272.0613. found: m/z 272.0603; $^1$H NMR (400 MHz, Acetone) δ 8.09 (d, J=8.24 Hz, 2H), 7.83 (dd, J=8.61, 15.20 Hz, 3H), 7.74 (d, J=15.20 Hz, 1H), 7.63-7.70 (m, 1H), 7.59 (t, J=7.69 Hz, 1H), 7.04 (d, J=8.61 Hz, 2H), 3.87 (s, 3H); $^{13}$C NMR (101 MHz, Acetone) δ 188.6, 163.4, 145.8, 141.3, 135.3, 133.3, 131.7, 131.4, 129.0, 128.5, 127.7, 120.0, 115.4, 55.9.

Compound 45: ((E)-1-(3-chlorophenyl)-3-(4-methoxyphenyl)prop-2-en-1-one): ESIMS m/z 273.02; $^1$H NMR (400 MHz, Acetone) δ 8.04-8.15 (m, 2H), 7.84 (d, J=15.57 Hz, 1H), 7.80 (d, J=15.57 Hz, 1H), 7.61-7.70 (m, 1H), 7.51-7.59 (m, 1H), 7.37 (t, J=7.51 Hz, 3H), 6.94-7.07 (m, 1H), 3.85 (s, 3H); $^{13}$C NMR (101 MHz, Acetone) δ 188.7, 161.1, 145.8, 140.6, 137.2, 135.3, 133.6, 131.3, 130.8, 129.2, 127.8, 122.7, 122.4, 117.6, 114.3, 55.6.

Compound 46: (E)-1-(4-chlorophenyl)-3-phenylprop-2-en-1-one; 4'-chlorochalcone.

Compound 47: ((E)-1-(4-chlorophenyl)-3-(4-methoxyphenyl)prop-2-en-1-one): ESIMS m/z 273.02; $^1$H NMR (400 MHz, Acetone) δ 8.08-8.19 (m, 2H), 7.75-7.86 (m, 3H), 7.67-7.75 (m, 1H), 7.52-7.62 (m, 2H), 7.01 (d, J=8.61 Hz, 2H), 3.86 (s, 3H); $^{13}$C NMR (101 MHz, Acetone) δ 188.7, 162.9, 145.4, 139.2, 138.0, 131.5, 131.1, 129.7, 128.5, 120.0, 115.3, 55.9.

Compound 48: ((E)-1-(2-bromophenyl)-3-phenylprop-2-en-1-one): $^1$H NMR (400 MHz, Acetone) δ 7.67-7.79 (m, 3H), 7.38-7.60 (m, 7H), 7.18 (d, J=16.12 Hz, 1H); $^{13}$C NMR (101 MHz, Acetone) δ 194.7, 147.1, 142.4, 135.5, 134.2, 132.5, 131.8, 130.1, 130.0, 129.6, 128.6, 127.1, 119.7.

Compound 49: ((E)-1-(3-bromophenyl)-3-phenylprop-2-en-1-one): EIMS m/z 286.96; $^1$H NMR (400 MHz, Acetone) δ 8.28 (t, J=1.65 Hz, 1H), 8.15 (d, J=7.88 Hz, 1H), 7.77-7.95 (m, 5H), 7.53 (t, J=7.88 Hz, 1H), 7.45-7.50 (m, 3H); $^{13}$C NMR (101 MHz, Acetone) δ 188.7, 145.8, 141.1, 136.5, 135.9, 132.1, 131.7, 131.6, 129.9, 129.8, 128.3, 123.4, 122.5.

Compound 50: ((E)-1-(4-bromophenyl)-3-phenylprop-2-en-1-one): EIMS m/z 286.96; $^1$H NMR (400 MHz, Acetone) δ 8.09 (d, J=8.43 Hz, 2H), 7.84 (s, 4H), 7.75 (d, J=8.61 Hz, 2H), 7.42-7.52 (m, 3H); $^{13}$C NMR (101 MHz, Acetone) δ 189.1, 145.5, 138.1, 136.1, 132.8, 131.6, 131.3, 129.9, 129.7, 128.1, 122.5.

Compound 51: ((E)-1-(2-iodophenyl)-3-phenylprop-2-en-1-one): EIMS m/z 333.96; $^1$H NMR (400 MHz, Acetone) δ 8.00 (d, J=7.88 Hz, 1H), 7.73 (t, J=3.66 Hz, 2H), 7.53-7.59 (m, 1H), 7.47-7.51 (m, 1H), 7.46 (d, J=2.20 Hz, 2H), 7.40-7.46 (m, 2H), 7.28 (dt, J=1.65, 7.60 Hz, 1H), 7.18 (d, J=16.12 Hz, 1H); $^{13}$C NMR (101 MHz, Acetone) δ 196.1, 147.3, 146.0, 140.9, 135.6, 132.3, 131.8, 130.0, 129.6, 129.4, 129.2, 126.6, 92.6.

Compound 52: ((E)-1-(2-iodophenyl)-3-(3-methoxyphenyl)prop-2-en-1-one): EIMS m/z 364.00; HREIMS: calcd for $C_{16}H_{13}O_2I$: 363.9942. found: m/z 363.9962; $^1$H NMR (400 MHz, Acetone) δ 8.00 (d, J=8.06 Hz, 1H), 7.56 (t, J=7.33 Hz, 1H), 7.48 (dd, J=1.50, 7.88 Hz, 1H), 7.41 (d, J=15.94 Hz, 1H), 7.35 (d, J=7.88 Hz, 1H), 7.23-7.33 (m, 3H), 7.18 (d, J=16.30 Hz, 1H), 7.03 (dd, J=2.02, 7.70 Hz, 1H), 3.81-3.88 (m, 3H); $^{13}$C NMR (101 MHz, Acetone) δ 196.2, 161.2, 147.3, 146.0, 140.9, 137.0, 132.3, 131.0, 129.4, 129.1, 126.9, 122.2, 118.0, 113.9, 92.6, 55.8.

Compound 53: ((E)-3-(4-(benzyloxy)phenyl)-1-(2-iodophenyl)prop-2-en-1-one): EIMS m/z 440.22; $^1$H NMR (400 MHz, Acetone) δ 7.99 (d, J=7.88 Hz, 1H), 7.69 (d, J=8.61 Hz, 2H), 7.55 (t, J=7.14 Hz, 1H), 7.48 (d, J=7.33 Hz, 2H), 7.45 (dd, J=1.47, 7.51 Hz, 1H), 7.39 (td, J=7.14, 15.94 Hz, 2H), 7.34 (br. s, 1H), 7.23-7.29 (m, 1H), 7.11 (d, J=8.24 Hz, 2H), 7.02 (t, J=15.39 Hz, 1H), 5.20 (s, 2H); $^{13}$C NMR (101 MHz, Acetone) δ 196.1, 162.2, 147.3, 146.3, 140.8, 137.9, 132.1, 131.5, 129.4, 129.3, 129.1, 128.9, 128.6, 128.4, 124.5, 116.3, 92.6, 70.7.

Compound 54: ((E)-3-(3-(benzyloxy)phenyl)-1-(2-iodophenyl)prop-2-en-1-one): EIMS m/z 440.22; $^1$H NMR (400 MHz, Acetone) δ 7.99 (dd, J=0.55, 7.88 Hz, 1H), 7.56 (dt, J=0.92, 7.69 Hz, 1H), 7.49 (ddd, J=1.47, 5.68, 6.59 Hz, 2H), 7.32-7.45 (m, 8H), 7.28-7.32 (m, 2H), 7.26 (dd, J=1.47, 7.51 Hz, 1H), 7.19 (d, J=16.12 Hz, 1H), 7.12 (dd, J=1.83, 7.69 Hz, 1H), 5.19 (s, 2H); $^{13}$C NMR (101 MHz, Acetone) δ 196.1, 160.3, 147.3, 146.0, 140.9, 138.2, 137.0, 132.3, 131.0, 129.4, 129.4, 129.2, 128.8, 128.6, 126.9, 122.6, 118.9, 114.9, 92.6, 70.6.

Compound 55: ((E)-1-(3-iodophenyl)-3-phenylprop-2-en-1-one): EIMS m/z 333.96; $^1$H NMR (400 MHz, Acetone) δ 8.46 (s, 1H), 8.17 (d, J=7.69 Hz, 1H), 8.02 (d, J=7.88 Hz, 1H), 7.86-7.90 (m, 1H), 7.79-7.83 (m, 1H), 7.74-7.94 (m, 2H), 7.43-7.54 (m, 3H), 7.38 (t, J=7.88 Hz, 1H); $^{13}$C NMR (101 MHz, Acetone) δ 188.7, 145.7, 142.5, 141.1, 138.1, 135.9, 131.6, 131.6, 129.9, 129.7, 128.7, 122.5, 95.0.

Compound 56: ((E)-1-(3-iodophenyl)-3-(4-methoxyphenyl)prop-2-en-1-one): HREIMS: calcd for $C_{16}H_{13}O_2I$: 363.9988. found: m/z 363.9958; $^1$H NMR (400 MHz, Acetone) δ 8.44 (br. t, J=1.00 Hz, 1H), 8.15 (d, J=7.88 Hz, 1H), 8.00 (d, J=7.88 Hz, 1H), 7.80 (dd, J=8.61, 15.57 Hz, 3H), 7.72 (d, J=15.57 Hz, 1H), 7.37 (t, J=7.88 Hz, 1H), 7.01 (d, J=8.79 Hz, 2H), 3.87 (s, 3H); $^{13}$C NMR (101 MHz, Acetone) δ 188.5, 163.0, 145.7, 142.2, 141.4, 138.0, 131.6, 131.6, 128.4, 128.6, 119.9, 115.2, 95.1, 55.9.

Compound 57: ((E)-1-(3-iodophenyl)-3-(3-methoxyphenyl)prop-2-en-1-one): EIMS m/z 364.00; HREIMS: calcd for $C_{16}H_{13}O_2I$: 363.9942. found: m/z 363.9962; $^1$H NMR (400 MHz, Acetone) δ 8.46 (t, J=1.65 Hz, 1H), 8.18 (d, J=8.43 Hz, 1H), 8.02 (d, J=7.69 Hz, 1H), 7.86 (d, J=15.57 Hz, 1H), 7.80 (d, J=15.39 Hz, 1H), 7.41 (s, 4H), 7.04 (td, J=2.01, 7.69 Hz, 1H), 3.87 (s, 3H); $^{13}$C NMR (101 MHz, Acetone) δ 188.7, 161.2, 145.7, 142.5, 141.1, 138.1, 137.3, 131.7, 130.9, 128.8, 122.7, 122.5, 117.6, 114.3, 95.0, 55.8.

Compound 58: ((E)-1-(4-iodophenyl)-3-phenylprop-2-en-1-one): EIMS m/z 333.96; $^1$H NMR (400 MHz, Acetone) δ 7.97 (dt, J=8.8, 1.6 Hz, 2H), 7.92 (dt, J=8.8, 1.6 Hz 2H), 7.8465 (d, J=15.6 Hz 1H), 7.7955 (d, J=15.6 Hz 1H), 7.82-7.85 (m, 3H), 7.45-7.48 (m, 3H); $^{13}$C NMR (101 MHz, Acetone) δ 190.0, 146.0, 139.5, 139.2, 136.5, 132.1, 131.6, 130.5, 130.2, 123.1, 101.6.

Compound 59: ((E)-1-(4-iodophenyl)-3-(4-methoxyphenyl)prop-2-en-1-one): ESIMS m/z 365.06; $^1$H NMR (400 MHz, Acetone) δ 7.94-8.05 (m, 2H), 7.86-7.93 (m, 2H), 7.79 (dd, J=8.61, 15.75 Hz, 3H), 7.62-7.74 (m, 1H), 7.02 (d, J=8.61 Hz, 2H), 3.87 (s, 3H); $^{13}$C NMR (101 MHz, Acetone) δ 189.1, 163.2, 145.3, 138.9, 136.9, 131.5, 131.0, 128.5, 120.0, 115.4, 99.6, 55.9.

Compound 60: ((E)-1-(4-iodophenyl)-3-(3-methoxyphenyl)prop-2-en-1-one): ESIMS m/z 365.06; HREIMS: calcd for $C_{16}H_{13}O_2I$: 363.9942. found: m/z 363.9962; $^1$H NMR (400 MHz, Acetone) δ 7.94-8.03 (m, 2H), 7.88-7.94 (m, 2H), 7.80-7.87 (m, 1H), 7.72-7.80 (m, 1H), 7.33-7.46 (m, J=7.51, 7.51, 8.61 Hz, 3H), 6.97-7.11 (m, 1H), 3.86 (s, 3H); $^{13}$C NMR (101 MHz, Acetone) δ 189.4, 161.2, 145.5, 138.9, 138.5, 137.3, 131.1, 130.9, 122.7, 122.3, 117.5, 114.3, 101.0, 55.8.

Experiment 2: Effect of Glucose Absorption in Adipocytes Enhanced by Chalcone Compounds 1 to 29.

For preliminarily testing the glucose absorption in adipocytes, a small scale of experiment was made using compounds 1-29. Please refer FIG. 1, which is a diagram showing the glucose absorption activity of adipocytes 3T3-L1 enhanced by the various chalcone compounds. After precursor adipocytes 3T3-L1 were induced as the matured adipocytes, culture medium with glucose (concentration of 300 mg/dl) and drugs were added, and the concentration of the remaining glucose in the culture medium were measured after 24 hours. Control was a group that only glucose was added without other drugs, and positive control was a group that the addition of insulin ($3.2 \times 10^{-7}$ M) or rosiglitazone (30 µg/ml) was made to compared with 29 chalcone compounds (30 µg/ml) prepared in Experiment 1. The results showed that compounds 12 and 26 had the best anti-hyperglycemic ability, had the similar anti-hyperglycemia efficacy as compared to rosiglitazone at the same dosage concentration, and didn't result in adipocyte death. Compounds 2, 3, 5 and 6 would lead to adipocyte death.

Please continuously refer to FIG. 1, glucose absorption activities of adipocytes enhanced by compound 9 and insulin respectively were relatively similar. Since compound 9 is the most basic structure in chalcone compounds and does not bind any substituent in ring A and ring B, it could be known that the basic skeleton of chalcone compound had ability to enhance glucose absorption. Comparing compound 9 with compounds 1, 2, 3, 4, 5 and 6 (hydroxy substituent(s) in ring A; methoxy or benzyloxy substituent in ring B), although compounds 1 to 6 had the various enhancements in glucose absorption, such activities in compounds 1 to 6 were not significantly better than that in compound 9. Compounds 2, 3, 5 and 6 were toxic to adipocytes at this drug concentration (data not shown), whereas compounds 1, 4 and 9 were non-toxic, suggesting that 4-hydroxy was one of the factors to affect the toxicity of chalcone compound.

Next, comparing compound 7 with compounds 8 and 9, the difference among three compounds lie in that 4'-methoxy and 3'-methoxy respectively were bound to ring B of compounds 7 and 8, whereas none of methoxy was bound to ring B of compound 9. Activity results showed that 4'-methoxy or 3'-methoxy in ring B of chalcone compound did not significantly affect the glucose absorption in cells. Comparing compound 10 (2-hydroxy in ring A) with compound 9, compound 10 did not show the higher glucose absorption in cells, indicating that 2-hydroxy of chalcone compound did not significantly affect the glucose absorption in cells. Comparing compound 1 (4'-methoxy in ring B) with compound 10, compound 1 did not show the higher glucose absorption in cells, indicating that 4'-methoxy of chalcone compound did not significantly affect the glucose absorption in cells. Comparing compound 11 (3'-benzyloxy in ring B) with compound 23 (4'-benzyloxy in ring B) and compound 10, the activity results showed that 3'-benzyloxy or 4'-benzyloxy in B ring of chalcone compound would enhance the glucose absorption in cells.

Comparing compounds 12, 13, 14, 16, 17 and 18 (bromide substituent in ring A; methoxy substituent in ring B), compound 12 has the best activity. Comparing compound 15 (3-chloride in ring A) with compound 16 (3-bromide in ring A), activities in both compounds were not significantly different, indicating that the chalcone compounds with 2-bromide in ring A and 4'-methoxy in ring B had the similar anti-hyperglycemic efficacy with rosiglitazone. Further comparing compounds 19, 20, 21, 22 and 23 (2-hydroxy and 5-bromide in ring A) with compound 12, the activity of compound 12 still was better than those of compounds 19 to 23, indicating that bromide must be bound to C-2 position of ring A to own the better activity regardless the substituent species and positional attachment in ring B.

In the end, comparing the activities of compounds 1, 7, 12, 26, 27 and 28 with different substituents at C-2 position of ring A and 4'-methoxy in ring B, the results showed that the activities influenced by the substituent at C-2 position of ring A were ranked as iodine>bromide>chloride>hydroxy=hydrogen>fluoride. It could be known that the chalcone compound with halide at C-2 position of ring A was determined to have the enhancement on the glucose absorption ability of cells via screening, and had the potential in regulating and stabilizing the glucose level in the blood of animals.

Experiment 3: Effect Analysis on Body Weight Gain of High-Fat Diet Induced Obesity and Glucose Resistance Mice Inhibited by Chalcone Compounds.

Figure 2:
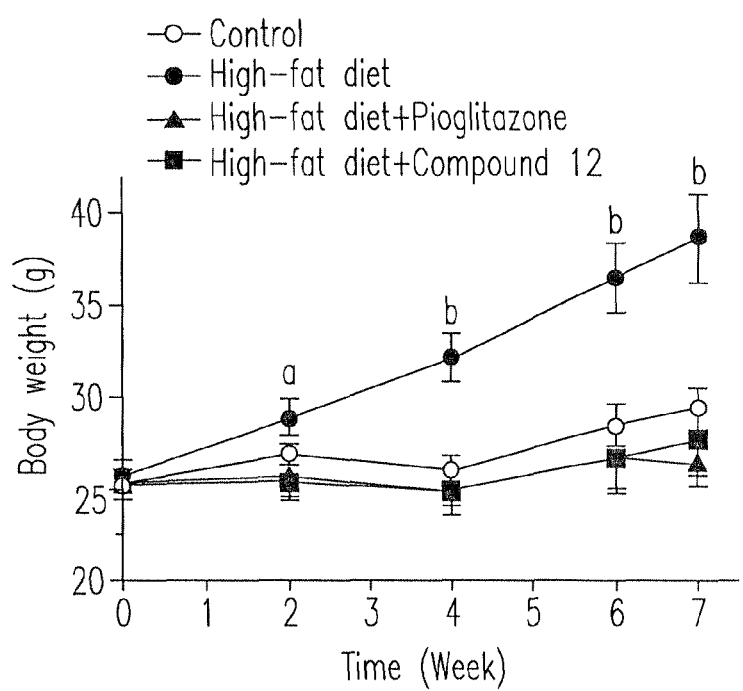
FIG. 2 is a diagram showing the body weight-time relationship of "high-fat (HF) diet" mice, and the body weights of mice are inhibited by chalcone compound 12 of the present invention. a ($p<0.01$) and b ($p<0.001$) respectively are statistically significant when group (d) (HF diet+compound 12) is compared with other three groups.

Please refer to FIG. 2, C57BL/6 mice were grouped as four groups. (a) "Control" group (normal healthy animal group): the mice were fed with normal feed. (b) "High-fat (HF) diet" group (unhealthy negative control group): the mice were fed with high-fat-percentage feed (at least 40% fat) for a long-term period for inducing obesity and metabolic syndromes. (c) "HF diet+pioglitazone" group (clinical administration control group): the mice were fed with high-fat-percentage feed (at least 40% fat) for a long-term period for inducing obesity and metabolic syndromes and simultaneously administered with the clinically anti-diabetes TZD, pioglitazone (oral dosage: 6.75 mg/kg/day). (d) "HF diet+compound 12" group: the mice were fed with high-fat-percentage feed (at least 40% fat) for a long-term period for inducing obesity and metabolic syndromes and simultaneously administered with the most effective chalcone compound 12 from Experiment 2 (oral dosage: 6.75 mg/kg/day, the same with pioglitazone in group (c) for comparison). The number of mice in the groups (a) to (d) were 5, 5, 6 and 13 respectively.

The body weights of mice in group (b) were significantly increased from the second week, as compared with other three groups. Comparing mice in group (d) with those in group (b), administration of compound 12 could significantly inhibit the body weight gain of mice. The body weights of mice in group (d) and group (c) did not show the significant difference, indicating that both of compound 12 and pioglitazone could inhibit the tendency of weight gain in HF diet mice.

Experiment 4: Effect Analysis on Blood Glucose Level and Anti-Glucose Intolerance of HF Diet Induced Obesity and Glucose Resistance Mice Regulated by Chalcone Compounds.

Figure 3A:
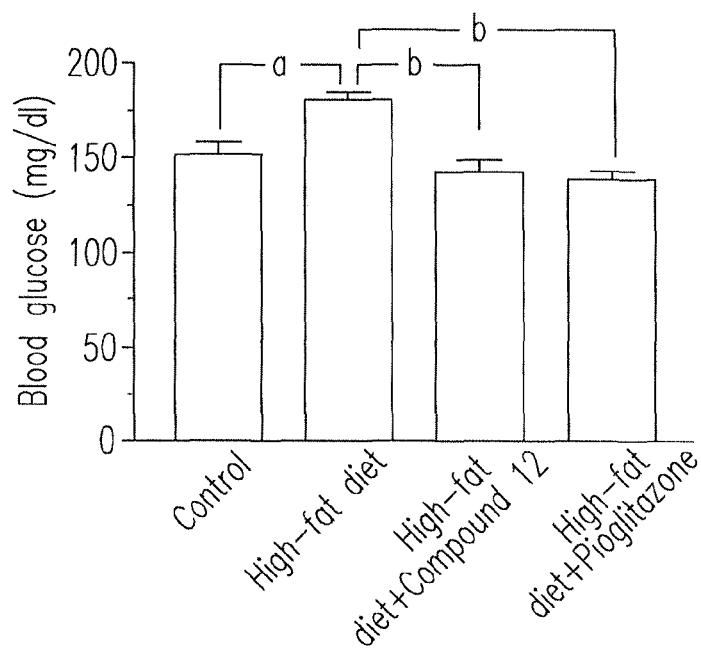
FIG. 3(a) is a diagram showing the inhibition of the blood glucose level in HF diet diabetic mice after the administration of chalcone compound 12 for 7 weeks. a ($p<0.05$) and b ($p<0.001$) respectively are statistically significant.
Figure 3B:
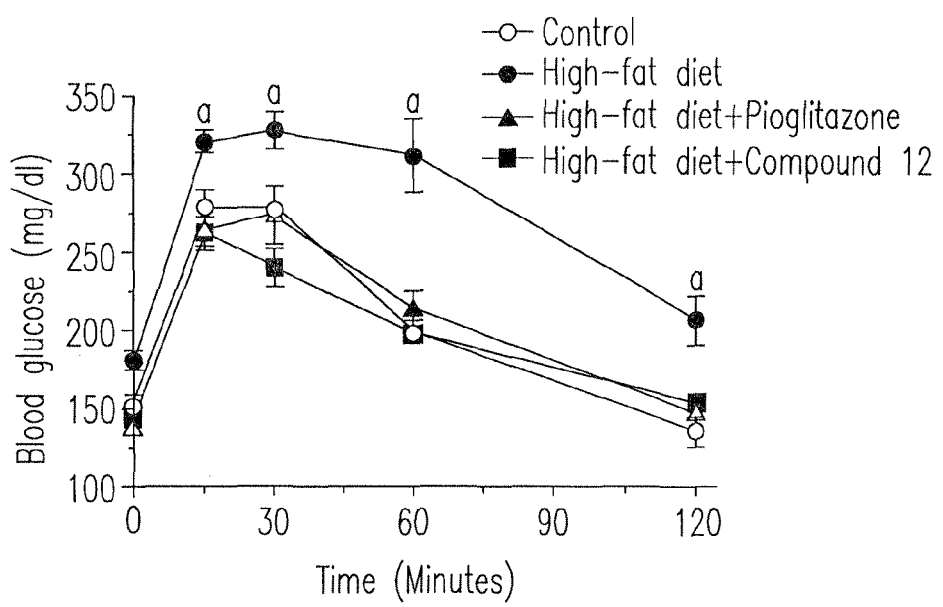
FIG. 3(b) is a diagram showing the inhibition of glucose intolerance in HF diet diabetic mice after the administration of chalcone compound 12 for 7 weeks. a ($p<0.001$) is statistically significant when the mice in "HF diet+compound 12" group are compared with those in other three groups.
Figure 4:
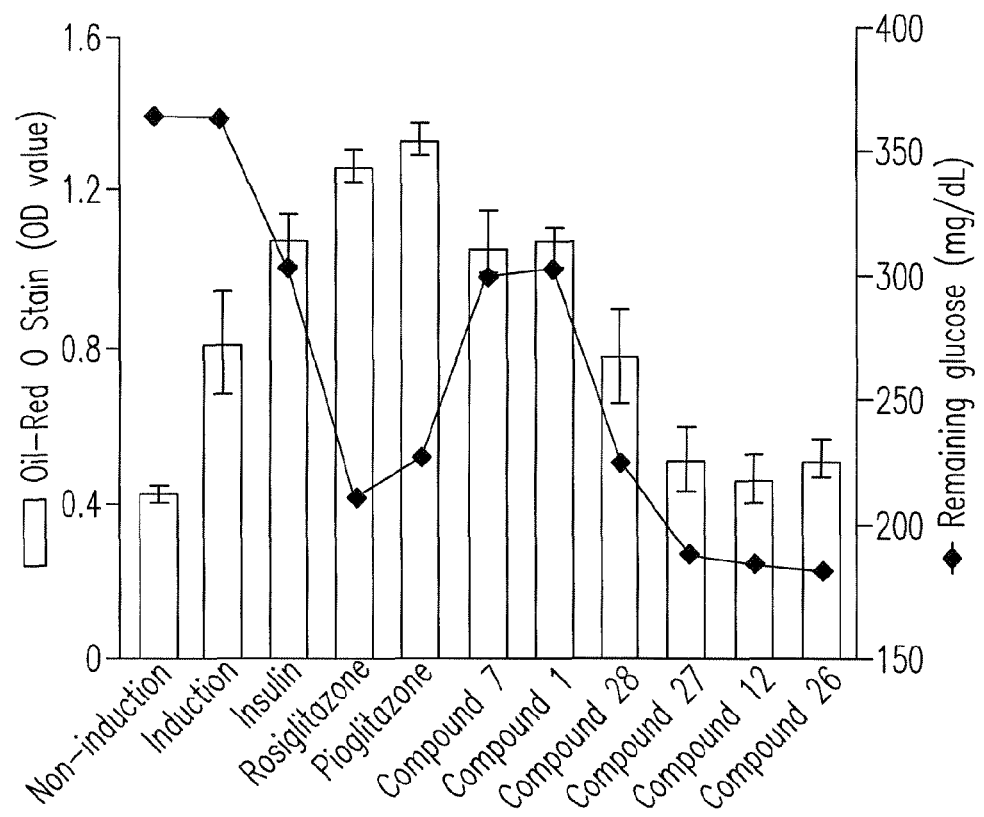
FIG. 4 is a diagram showing the Oil-red O staining and the remaining glucose of insulin, rosiglitazone, pioglitazone and chalcone derivatives on lipid droplet formation in 3T3-L1 adipocytes.

The numbers of mice in Experiment 4 were the same as in Experiment 3, and mice were divided as four groups, "control", "HF diet", "HF diet+pioglitazone" and "HF diet+compound 12" groups. Please refer to FIG. 3(a), the fasting blood glucose level of HF diet mice at the seventh week had increased to 175 mg/dl, and the phenomenon of impaired glucose tolerance occurred. Please refer to FIG. 3(a), comparing mice in "HF diet+compound 12" group with those in "HF diet" group, compound 12 could significantly inhibit the increase of blood glucose level in mice, the effect was similar to the mice in "HF diet+pioglitazone" group, and dangerousless hypoglycemic state occurred. Please refer to FIG. 3(b), in the oral glucose tolerance test (OGTT), compound 12 could significantly inhibit the occurrence of glucose intolerance in HF diet mice.

Experiment 5: In Vitro Anti-Diabetic Screening Model Based on Glucose Consumption.

Based on the results of Experiments 2-4, it is supposed that the chalcone compounds with a halogen substituent in ring A own the better glucose utilization that those without a halogen substituent in ring A. Thus, more chalcone compounds with the various substituents in ring A and/or ring B were prepared for further comparison, so that the chalcone compounds prepared in the invention were demonstrated to be beneficial in treating diabetes and metabolic syndromes.

Adipose tissues are major sites for postprandial glucose uptake. Therefore, in vitro anti-diabetic screening model based on measuring glucose consumption after 24 hours in culture medium of 3T3-L1 adipocytes was developed. In our preliminary screening results as described in Table 1, it was found that the substitution on A-ring is crucial for promoting cellular glucose consumption. Accordingly, 60 chalcone derivatives with and without substitutions on A-ring were examined in our developed model. Two anti-diabetic clinical drugs, pioglitazone and rosiglitazone were used as positive controls with culture medium glucose concentrations of 230 and 263 mg/dl, respectively. Chalcones which lowered glucose level (n=3) below 240 mg/dl were regarded as active candidates (referring to Table 1). Structure-activity relationship (SAR) analyses data are also determined. Chalcones with hydroxy (compound 36), chloro (compound 27), bromo (compound 12) and iodo (compounds 51, 26 and 52) substitutions at position 2 on A-ring exhibited good activity with culture glucose medium concentrations ranging from 210 to 236 mg/dl. Additionally, chalcones with iodo substitution at position 3 on A-ring (compounds 54 and 56) were active with comparable results (238 and 233 mg/dl, respectively). It is noteworthy to state that methoxy or benzyloxy substitution on B ring also positively affected chalcones activity (compounds 36, 37, 48, 12, 13, 56 and 57).

TABLE 1

Chalcone derivatives and the value of glucose consumption in culture media

| Compound | A-Ring | | | | B-Ring | | | Glucose (mg/dl)[a] |
| --- | --- | --- | --- | --- | --- | --- | --- | --- |
| | 2 | 3 | 4 | 5 | 3' | 4' | 5' | |
| 1 | OH | H | H | H | H | OCH$_3$ | H | 283 ± 21.4 |
| 2 | OH | H | OH | H | H | H | H | 273 ± 2.9 |
| 3 | OH | H | OH | H | H | OCH$_2$C$_6$H$_5$ | H | 249 ± 12.2 |
| 4 | OH | H | H | H | H | H | OCH$_3$ | 264 ± 7.8 |
| 5 | OH | H | OH | H | H | OCH$_3$ | H | 248 ± 0.4 |
| 6 | OH | H | OH | H | H | H | OCH$_3$ | 274 ± 12.1 |
| 7 | H | H | H | H | H | OCH$_3$ | H | 261 ± 3.2 |
| 8 | H | H | H | H | H | H | OCH$_3$ | 261 ± 7.2 |
| 9 | H | H | H | H | H | H | H | 253 ± 9.9 |
| 10 | OH | H | H | H | H | H | H | 269 ± 11.0 |
| 11 | OH | H | H | H | H | H | OCH$_2$C$_6$H$_5$ | 256 ± 13.1 |
| 12 | Br | H | H | H | H | OCH$_3$ | H | 230 ± 8.7 |
| 13 | Br | H | H | H | H | H | OCH$_3$ | 249 ± 5.2 |
| 14 | H | Br | H | H | H | H | OCH$_3$ | 262 ± 2.2 |
| 15 | H | H | Cl | H | H | H | OCH$_3$ | 272 ± 22.4 |
| 16 | H | H | Br | H | H | H | OCH$_3$ | 257 ± 10.0 |
| 17 | H | Br | H | H | H | OCH$_3$ | H | 248 ± 8.0 |
| 18 | H | H | Br | H | H | OCH$_3$ | H | 261 ± 12.7 |
| 19 | OH | H | H | Br | H | H | H | 253 ± 7.8 |
| 20 | OH | H | H | Br | H | OCH$_3$ | H | 254 ± 17.6 |
| 21 | OH | H | H | Br | H | H | OCH$_3$ | 260 ± 3.3 |
| 22 | OH | H | H | Br | H | H | OCH$_2$C$_6$H$_5$ | 252 ± 0.1 |
| 23 | OH | H | H | Br | H | OCH$_2$C$_6$H$_5$ | H | 256 ± 1.3 |
| 24 | OH | H | H | H | H | H | OH | 267 ± 3.4 |
| 25 | OH | H | H | H | H | OCH$_2$C$_6$H$_5$ | H | 260 ± 3.8 |
| 26 | I | H | H | H | H | OCH$_3$ | H | 210 ± 3.7 |
| 27 | Cl | H | H | H | H | OCH$_3$ | H | 234 ± 24.4 |
| 28 | F | H | H | H | H | OCH$_3$ | H | 259 ± 0.3 |
| 29 | H | H | H | H | H | OH | H | 263 ± 5.6 |
| 30 | H | H | H | H | OCH$_2$C$_6$H$_5$ | H | H | 285 ± 8.2 |
| 31 | H | H | H | H | H | OCH$_2$C$_6$H$_5$ | H | 274 ± 13.0 |
| 32 | H | H | H | H | H | —OCH$_2$O— | | 252 ± 18.1 |
| 33 | OH | H | H | H | H | —OCH$_2$O— | | 279 ± 7.6 |
| 34 | OH | H | OH | H | OCH$_2$C$_6$H$_5$ | H | H | 283 ± 2.6 |
| 35 | OH | H | H | F | OCH$_3$ | H | H | 297 ± 9.3 |
| 36 | OH | H | H | Cl | H | H | H | 236 ± 17.5 |
| 37 | OH | H | H | Cl | H | OCH$_3$ | H | 282 ± 16.4 |
| 38 | OH | H | H | Br | OCH$_3$ | H | H | 266 ± 23.3 |
| 39 | F | H | H | H | OCH$_3$ | H | H | 285 ± 4.4 |
| 40 | H | F | H | H | H | OCH$_3$ | H | 298 ± 15.5 |
| 41 | H | F | H | H | OCH$_3$ | H | H | 282 ± 10.1 |
| 42 | H | H | F | H | OCH$_3$ | H | H | 285 ± 1.6 |
| 43 | H | Cl | H | H | H | H | H | 291 ± 9.2 |
| 44 | H | Cl | H | H | H | OCH$_3$ | H | 287 ± 13.4 |
| 45 | H | Cl | H | H | OCH$_3$ | H | H | 255 ± 27.1 |
| 46 | H | H | Cl | H | H | H | H | 295 ± 8.8 |
| 47 | H | H | Cl | H | H | OCH$_3$ | H | 293 ± 7.8 |
| 48 | Br | H | H | H | H | H | H | 249 ± 20.8 |
| 49 | H | Br | H | H | H | H | H | 299 ± 7.3 |
| 50 | H | H | Br | H | H | H | H | 295 ± 5.8 |
| 51 | I | H | H | H | H | H | H | 223 ± 13.8 |
| 52 | I | H | H | H | OCH$_3$ | H | H | 210 ± 2.0 |
| 53 | I | H | H | H | H | OCH$_2$C$_6$H$_5$ | H | 249 ± 3.6 |
| 54 | H | I | H | H | OCH$_2$C$_6$H$_5$ | H | H | 238 ± 1.1 |
| 55 | H | I | H | H | H | H | H | 294 ± 7.3 |
| 56 | H | I | H | H | H | OCH$_3$ | H | 233 ± 3.5 |
| 57 | H | I | H | H | OCH$_3$ | H | H | 246 ± 11.3 |
| 58 | H | H | I | H | H | H | H | 292 ± 5.3 |
| 59 | H | H | I | H | H | OCH$_3$ | H | 299 ± 3.8 |
| 60 | H | H | I | H | OCH$_3$ | H | H | 274 ± 22.5 |
| Control | | | | | | | | 310 ± 4.0 |
| Insulin (3.2 × 10$^{-17}$M) | | | | | | | | 294 ± 6.3 |
| Rosiglitazone[b] | | | | | | | | 263 ± 23.9 |
| Pioglitazone[b] | | | | | | | | 230 ± 13.5 |

[a]Data are means ± SD of N = 3 determinations.
[b]Chalcone derivatives, rosiglitazone and piolitazone were using the same concentrations 30 μg/ml.

Experiment 6: Effects of Insulin, Rosiglitazone, Pioglitazone and Chalcone Derivatives on Lipid Droplet Formation in 3T3-L1 Adipocytes.

After two days of differentiation, 3T3-L1 cells were treated without (control) or with insulin (3.2×10$^{-7}$ M), RSZ (30 μg/ml), PIO (30 μg/ml), and chalcone derivatives (30 μg/ml)

in DMEM containing 25 mM D-glucose. After 4 days, lipid droplets were observed by Oil-Red O staining (data not shown). The result demonstrates that compounds 12 and 26 significantly prevent the formation of lipid droplets (red color). In contrast, insulin, pioglitazone and rosiglitazone promote glucose consumption but also increase the lipid droplets in adipocytes. This result indicates a very distinct pharmacological pathway of compounds 12 and 26.

Experiment 7: Effect Analysis on Body Weight Gain and Blood Glucose Level of HF Diet Induced Obesity and Glucose Resistance Mice Inhibited by Chalcone Compound 26.

Figure 5:
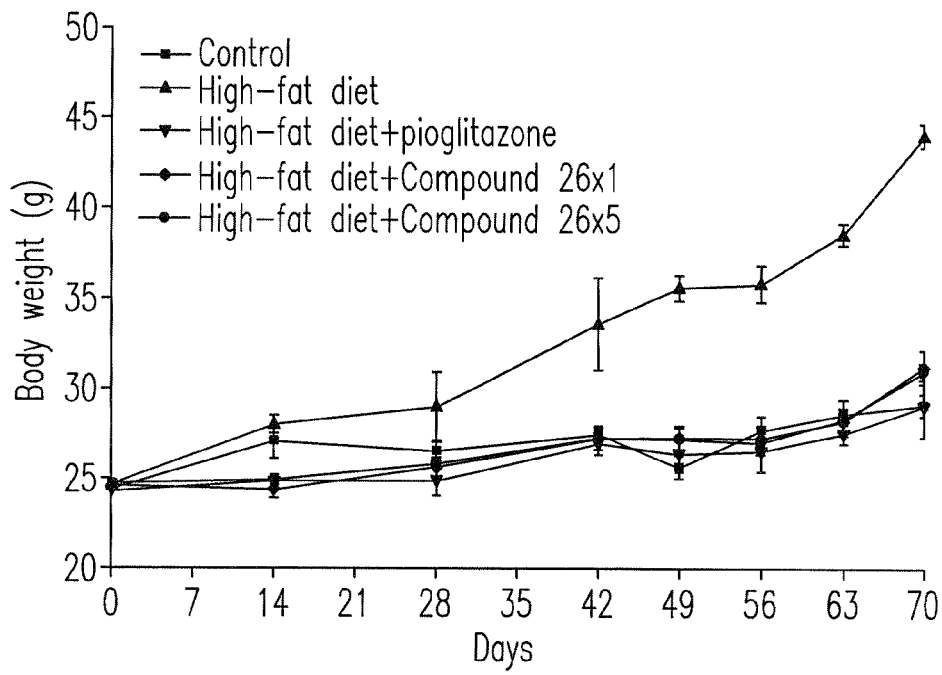
FIG. 5 is a diagram showing the body weight-time relationship of "HF diet" mice fed with compound 26, and the body weights of mice are inhibited by compound 26 of the present invention.
Figure 6:
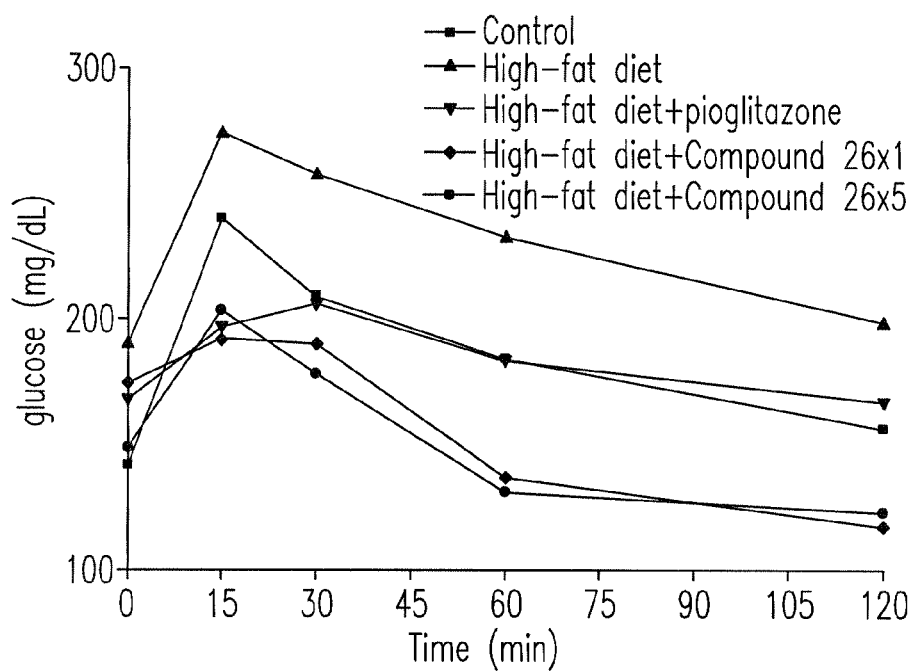
FIG. 6 is a diagram showing the inhibition of glucose intolerance in HF diet diabetic mice after the administration of compound 26 for 7 weeks.

The method and conditions for performing Experiment 7 were similar to those in Experiments 3 and 4, wherein C57BL/6 mice were grouped as five groups, (a) "Control" group (n=6), (b) "HF diet" group (n=7); (c) "HF diet+pioglitazone" group (oral dosage: 6.75 mg/kg/day pioglitazone, n=8); (d) "HF diet+compound 26×1" group: the mice were fed with high-fat-percentage feed (at least 40% fat) for a long-term period for inducing obesity and metabolic syndromes and simultaneously administered with compound 26 (oral dosage: 6.75 mg/kg/day, n=11); and (e) "HF diet+compound 26×5" group (oral dosage: 33.75 mg/kg/day compound 26, n=12). Please refer to FIGS. 5 and 6, the results demonstrated that compound 26 significantly prevents obesity and insulin resistance.

In concluding the results of in vitro and in vivo activity tests from Experiments 1 to 7, the halide-bound chalcone compound could regulate and stabilize blood glucose level in cells or animals, and inhibit the occurrence of impaired glucose tolerance and the abrupt rise of body weight in animals which were fed with HF diet for a long-term period. At the same time, no toxic response was found in mice within the experimental period of at least seven week administration, the liver-kidney evaluation indexes (glutamic pyruvic transaminase (GPT), creatinine) of mice also were regular.

Therefore, the halide-bound chalcone compounds of the present invention can replace the commercial medicines with severe side effects, to be developed as the novel and effective drugs for treating and controlling diabetes, body weight and metabolic syndromes.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A composition for treating one of a diabetes and a metabolic syndrome, comprising a chalcone compound represented by formula I:

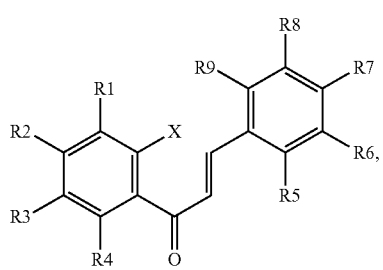

(I)

wherein X is one of a bromide and an iodine, each of R1, R2, R3 and R4 is selected from a group consisting of a first hydrogen, a first hydroxide and a halogen, and each of R5, R6, R7, R8 and R9 is selected from a group consisting of a second hydrogen, a second hydroxide, a $C_1$ to $C_{20}$ alkoxy group and a benzyloxy group.

2. The composition according to claim 1, wherein the halogen is selected from a group consisting of a fluoride, a chloride, a bromide and an iodine.

3. The composition according to claim 1, wherein one of the diabetes and the metabolic syndrome occurs in a subject.

4. The composition according to claim 3, wherein the subject is one of a human being and a rodent.

5. The composition according to claim 3, wherein the subject has a blood glucose value, and the composition is effective in at least one treatment of regulating the blood glucose value and stabilizing the blood glucose value.

6. The composition according to claim 3, wherein the subject is subjected to at least one of an impaired glucose tolerance and a body weight gain, and the composition is effective in inhibiting at least one of the impaired glucose tolerance, the body weight gain and the accumulation of lipid droplets in adipocytes.

7. The composition according to claim 1 further being effective in at least one treatment of inhibiting the metabolic syndrome and delaying the metabolic syndrome.

8. A composition for inhibiting a body weight gain, comprising a chalcone compound represented by formula I:

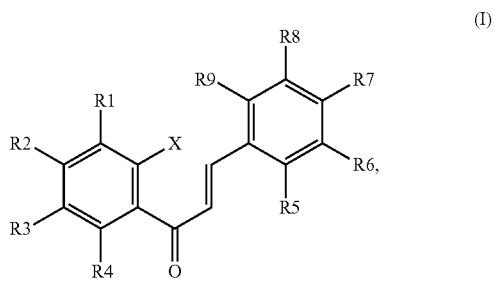

(I)

wherein X is one of a bromide and an iodine, each of R1, R2, R3 and R4 is selected from a group consisting of a first hydrogen, a first hydroxide and a halogen, and each of R5, R6, R7, R8 and R9 is selected from a group consisting of a second hydrogen, a second hydroxide, a $C_1$ to $C_{20}$ alkoxy group and a benzyloxy group.

9. The composition according to claim 8, wherein the body weight gain occurs in a subject.

10. The composition according to claim 9, wherein the subject is a mouse being continuously fed with a high fat diet and subjected to an impaired glucose intolerance, and the high fat diet has at least 40 weight percentage of fat.

11. The composition according to claim 9, wherein the subject has adipocytes, and the composition is used to inhibit the accumulation of lipid droplets in the adipocytes.

* * * * *